(12) United States Patent
Thompson et al.

(10) Patent No.: US 11,324,620 B2
(45) Date of Patent: May 10, 2022

(54) SYSTEMS AND METHODS FOR MEASURING VOLUME OF POTENTIAL SLEEVE IN A SLEEVE GASTRECTOMY

(71) Applicant: Standard Bariatrics, Inc., Cincinnati, OH (US)

(72) Inventors: Jonathan Thompson, Cincinnati, OH (US); Mark Steven Ortiz, Milford, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 537 days.

(21) Appl. No.: 16/372,212

(22) Filed: Apr. 1, 2019

(65) Prior Publication Data

US 2019/0224029 A1 Jul. 25, 2019

Related U.S. Application Data

(63) Continuation of application No. 15/267,414, filed on Sep. 16, 2016, now Pat. No. 10,285,837.
(Continued)

(51) Int. Cl.
*A61F 5/00* (2006.01)
*A61B 17/12* (2006.01)
(Continued)

(52) U.S. Cl.
CPC .......... *A61F 5/0086* (2013.01); *A61B 17/122* (2013.01); *A61B 17/128* (2013.01);
(Continued)

(58) Field of Classification Search
CPC ...... A61F 5/0076; A61F 5/0086; A61F 5/003; A61F 5/0069; A61F 5/0089;
(Continued)

(56) References Cited

U.S. PATENT DOCUMENTS

| 848,126 A | 3/1907 | Roosevelt |
| 1,413,896 A | 4/1922 | Brix |

(Continued)

FOREIGN PATENT DOCUMENTS

| CA | 2663002 A1 | 10/2009 |
| EP | 0140552 A2 | 5/1985 |

(Continued)

OTHER PUBLICATIONS

Geoffrey Parker, A New Stomach Clamp, 26 Postgrad Med. J. 550; 1 page.
(Continued)

*Primary Examiner* — Philip R Wiest
(74) *Attorney, Agent, or Firm* — Ulmer & Berne LLP

(57) ABSTRACT

One or more medical devices may be provided that may be used, for example, in bariatric surgery including a vertical sleeve gastrectomy. Occlusion devices can be integrated with a catheter or tube to occlude one or more proximal or distal landmarks of a stomach and a stapling guide may be used to occlude a lateral boundary of the stomach to define a cavity. A volume of the potential resultant sleeve may be determined by inserting fluid or gas into the catheter or tube, measuring pressure, and calculating the volume of the cavity.

17 Claims, 6 Drawing Sheets

Related U.S. Application Data

(60) Provisional application No. 62/219,564, filed on Sep. 16, 2015.

(51) Int. Cl.
| | |
|---|---|
| *A61B 17/122* | (2006.01) |
| *A61B 17/128* | (2006.01) |
| *A61B 17/00* | (2006.01) |
| *A61B 17/072* | (2006.01) |
| *A61B 90/00* | (2016.01) |

(52) U.S. Cl.
CPC .. *A61B 17/12099* (2013.01); *A61B 17/12136* (2013.01); *A61F 5/003* (2013.01); *A61F 5/0069* (2013.01); *A61F 5/0076* (2013.01); *A61F 5/0089* (2013.01); *A61B 17/07207* (2013.01); *A61B 17/12009* (2013.01); *A61B 17/1227* (2013.01); *A61B 2017/00818* (2013.01); *A61B 2090/064* (2016.02); *A61F 2220/0066* (2013.01); *A61F 2220/0075* (2013.01); *A61F 2220/0091* (2013.01); *A61F 2230/0069* (2013.01)

(58) Field of Classification Search
CPC ...... A61F 2220/0066; A61F 2220/0075; A61F 2220/0091; A61F 2230/0069; A61B 17/12099; A61B 17/12136; A61B 17/122; A61B 17/128; A61B 17/12009; A61B 17/1227; A61B 2017/00818
See application file for complete search history.

(56) References Cited

U.S. PATENT DOCUMENTS

| | | |
|---|---|---|
| 2,659,371 A | 11/1953 | Schnee |
| 2,686,520 A | 8/1954 | Jarvis et al. |
| 3,017,637 A | 1/1962 | Sampson |
| 3,490,675 A | 1/1970 | Green et al. |
| 3,551,987 A | 1/1971 | Wilkinson |
| 3,877,434 A | 4/1975 | Ferguson et al. |
| 4,216,891 A | 8/1980 | Behlke |
| 4,269,190 A | 5/1981 | Behney |
| 4,319,576 A | 3/1982 | Rothfuss |
| 4,354,628 A | 10/1982 | Green |
| 4,442,964 A | 4/1984 | Becht |
| 4,458,681 A | 7/1984 | Hopkins |
| 4,494,057 A | 1/1985 | Hotta |
| 4,520,817 A | 6/1985 | Green |
| 4,527,724 A | 7/1985 | Chow et al. |
| 4,558,699 A | 12/1985 | Bashour |
| 4,605,001 A | 8/1986 | Rothfuss et al. |
| 4,605,004 A | 8/1986 | Di Giovanni et al. |
| 4,608,981 A | 9/1986 | Rothfuss et al. |
| 4,610,383 A | 9/1986 | Rothfuss et al. |
| 4,632,290 A | 12/1986 | Green et al. |
| 4,633,861 A | 1/1987 | Chow et al. |
| 4,676,774 A | 6/1987 | Semm et al. |
| 4,679,557 A | 7/1987 | Opie et al. |
| 4,705,038 A | 11/1987 | Sjostrom et al. |
| 4,784,137 A | 11/1988 | Kulik et al. |
| 4,803,985 A | 2/1989 | Hill |
| 4,819,853 A | 4/1989 | Green |
| 4,848,637 A | 7/1989 | Pruitt |
| 4,930,503 A | 6/1990 | Pruitt |
| 4,941,623 A | 7/1990 | Pruitt |
| 4,951,861 A | 8/1990 | Schulze et al. |
| 4,976,721 A | 12/1990 | Blasnik et al. |
| 4,978,049 A | 12/1990 | Green |
| 5,040,715 A | 8/1991 | Green et al. |
| 5,136,220 A | 8/1992 | Philipp |
| 5,152,744 A | 10/1992 | Krause et al. |
| 5,176,651 A | 1/1993 | Allgood et al. |
| 5,205,459 A | 4/1993 | Brinkerhoff et al. |
| 5,219,111 A | 6/1993 | Bilotti et al. |
| 5,221,036 A | 6/1993 | Takase |
| 5,222,961 A | 6/1993 | Nakao et al. |
| 5,258,009 A | 11/1993 | Conners |
| 5,307,976 A | 5/1994 | Olson |
| 5,308,576 A | 5/1994 | Green et al. |
| 5,312,410 A | 5/1994 | Miller et al. |
| 5,327,914 A | 7/1994 | Shlain |
| 5,333,772 A | 8/1994 | Rothfuss et al. |
| 5,345,949 A | 9/1994 | Shlain |
| 5,389,098 A | 2/1995 | Tsuruta et al. |
| 5,395,030 A | 3/1995 | Kuramoto et al. |
| 5,395,034 A | 3/1995 | Allen et al. |
| 5,413,267 A | 5/1995 | Solyntjes et al. |
| 5,415,334 A | 5/1995 | Williamson, IV et al. |
| 5,431,323 A | 7/1995 | Smith et al. |
| 5,443,475 A | 8/1995 | Auerbach et al. |
| 5,452,836 A | 9/1995 | Huitema et al. |
| 5,452,837 A | 9/1995 | Williamson, IV et al. |
| 5,456,401 A | 10/1995 | Green et al. |
| 5,465,895 A | 11/1995 | Knodel et al. |
| 5,465,896 A | 11/1995 | Allen et al. |
| 5,469,840 A | 11/1995 | Tanii et al. |
| 5,470,006 A | 11/1995 | Rodak |
| 5,470,009 A | 11/1995 | Rodak |
| 5,480,089 A | 1/1996 | Blewett |
| 5,485,952 A | 1/1996 | Fontayne |
| 5,487,500 A | 1/1996 | Knodel et al. |
| 5,496,333 A | 3/1996 | Sackier et al. |
| 5,503,638 A | 4/1996 | Cooper et al. |
| 5,507,426 A | 4/1996 | Young et al. |
| 5,507,773 A | 4/1996 | Huitema et al. |
| 5,514,098 A | 5/1996 | Pfoslgraf et al. |
| 5,531,744 A | 7/1996 | Nardella et al. |
| 5,549,621 A | 8/1996 | Bessler et al. |
| 5,551,622 A | 9/1996 | Yoon |
| 5,554,169 A | 9/1996 | Green et al. |
| 5,560,530 A | 10/1996 | Bolanos et al. |
| 5,562,702 A | 10/1996 | Huitema et al. |
| 5,571,116 A | 11/1996 | Bolanos et al. |
| 5,571,131 A | 11/1996 | Ek et al. |
| 5,586,711 A | 12/1996 | Ley et al. |
| 5,597,107 A | 1/1997 | Knodel et al. |
| 5,630,540 A | 5/1997 | Blewett |
| 5,632,432 A | 5/1997 | Schulze et al. |
| 5,636,780 A | 6/1997 | Green et al. |
| 5,662,667 A | 9/1997 | Knodel |
| 5,676,674 A | 10/1997 | Bolanos et al. |
| 5,689,159 A | 11/1997 | Culp et al. |
| 5,697,542 A | 12/1997 | Knodel et al. |
| 5,702,409 A | 12/1997 | Rayburn et al. |
| 5,704,534 A | 1/1998 | Huitema et al. |
| 5,732,871 A | 3/1998 | Clark et al. |
| 5,762,256 A | 6/1998 | Mastri et al. |
| 5,779,130 A | 7/1998 | Alesi et al. |
| 5,779,132 A | 7/1998 | Knodel et al. |
| 5,782,396 A | 7/1998 | Mastri et al. |
| 5,797,538 A | 8/1998 | Heaton et al. |
| 5,810,240 A | 9/1998 | Robertson |
| 5,814,055 A | 9/1998 | Knodel et al. |
| 5,819,240 A | 10/1998 | Kara |
| 5,820,009 A | 10/1998 | Melling et al. |
| 5,865,361 A | 2/1999 | Milliman et al. |
| 5,868,760 A | 2/1999 | McGuckin, Jr. |
| 5,871,135 A | 2/1999 | Williamson IV et al. |
| 5,901,895 A | 5/1999 | Heaton et al. |
| 5,902,312 A | 5/1999 | Frater et al. |
| 5,954,259 A | 9/1999 | Viola et al. |
| 5,964,394 A | 10/1999 | Robertson |
| 5,980,248 A | 11/1999 | Kusakabe et al. |
| 5,988,479 A | 11/1999 | Palmer |
| 6,032,849 A | 3/2000 | Mastri et al. |
| 6,048,330 A | 4/2000 | Atala |
| 6,099,551 A | 8/2000 | Gabbay |
| 6,264,087 B1 | 7/2001 | Whitman |
| 6,270,507 B1 | 8/2001 | Callicrate |
| 6,315,184 B1 | 11/2001 | Whitman |
| 6,325,810 B1 | 12/2001 | Hamilton et al. |
| 6,488,196 B1 | 12/2002 | Fenton |

(56) References Cited

U.S. PATENT DOCUMENTS

| | | |
|---|---|---|
| 6,505,768 B2 | 1/2003 | Whitman |
| 6,511,490 B2 | 1/2003 | Robert |
| 6,616,446 B1 | 9/2003 | Schmid |
| 6,716,233 B1 | 4/2004 | Whitman |
| 6,793,652 B1 | 9/2004 | Whitman et al. |
| 6,835,199 B2 | 12/2004 | McGuckin et al. |
| RE38,708 E | 3/2005 | Bolanos et al. |
| 6,953,138 B1 | 10/2005 | Dworak et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,025,791 B2 | 4/2006 | Levine et al. |
| 7,032,799 B2 | 4/2006 | Viola et al. |
| 7,037,344 B2 | 5/2006 | Kagan et al. |
| 7,044,353 B2 | 5/2006 | Mastri et al. |
| 7,070,083 B2 | 7/2006 | Jankowski |
| 7,128,253 B2 | 10/2006 | Mastri et al. |
| 7,134,587 B2 | 11/2006 | Schwemberger et al. |
| 7,175,648 B2 | 2/2007 | Nakao |
| 7,207,472 B2 | 4/2007 | Wukusick et al. |
| 7,225,964 B2 | 6/2007 | Mastri et al. |
| 7,229,428 B2 | 6/2007 | Gannoe et al. |
| 7,235,089 B1 | 6/2007 | McGuckin, Jr. |
| 7,258,262 B2 | 8/2007 | Mastri et al. |
| 7,288,100 B2 | 8/2007 | Molina Trigueros |
| 7,278,562 B2 | 10/2007 | Mastri et al. |
| 7,278,563 B1 | 10/2007 | Green |
| 7,308,998 B2 | 12/2007 | Mastri et al. |
| RE40,237 E | 4/2008 | Bilotti et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,076 B2 | 8/2008 | Racenet et al. |
| 7,422,138 B2 | 9/2008 | Bilotti et al. |
| 7,434,716 B2 | 10/2008 | Viola |
| 7,434,717 B2 | 10/2008 | Shelton, IV et al. |
| 7,438,209 B1 | 10/2008 | Hess et al. |
| 7,455,676 B2 | 11/2008 | Holsten et al. |
| 7,467,740 B2 | 12/2008 | Shelton, IV et al. |
| 7,472,815 B2 | 1/2009 | Shelton, IV et al. |
| 7,481,349 B2 | 1/2009 | Holsten et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,564 B2 | 6/2009 | Boudreaux |
| 7,549,654 B2 | 6/2009 | Boudreaux |
| 7,565,993 B2 | 7/2009 | Milliman et al. |
| 7,588,175 B2 | 9/2009 | Timm et al. |
| 7,588,176 B2 | 9/2009 | Timm et al. |
| 7,588,177 B2 | 9/2009 | Racenet |
| 7,604,151 B2 | 10/2009 | Hess et al. |
| 7,617,961 B2 | 11/2009 | Viola |
| 7,635,074 B2 | 12/2009 | Olson et al. |
| 7,641,091 B2 | 1/2010 | Olson et al. |
| 7,645,285 B2 | 1/2010 | Cosgrove et al. |
| 7,658,312 B2 | 2/2010 | Vidal et al. |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,673,781 B2 | 3/2010 | Swayze et al. |
| 7,673,782 B2 | 3/2010 | Hess et al. |
| 7,690,547 B2 | 4/2010 | Racenet et al. |
| 7,694,864 B2 | 4/2010 | Okada et al. |
| 7,704,264 B2 | 4/2010 | Ewers et al. |
| 7,708,684 B2 | 5/2010 | Demarais et al. |
| 7,717,312 B2 | 5/2010 | Beetel |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,744,613 B2 | 6/2010 | Ewers et al. |
| 7,758,493 B2 | 7/2010 | Gingras |
| 7,770,774 B2 | 8/2010 | Mastri et al. |
| 7,775,967 B2 | 8/2010 | Gertner |
| D624,182 S | 9/2010 | Thouement |
| 7,793,812 B2 | 9/2010 | Moore et al. |
| 7,794,475 B2 | 9/2010 | Hess et al. |
| 7,815,092 B2 | 10/2010 | Whitman et al. |
| 7,819,896 B2 | 10/2010 | Racenet |
| 7,828,188 B2 | 11/2010 | Jankowski |
| 7,837,079 B2 | 11/2010 | Holsten et al. |
| 7,846,149 B2 | 12/2010 | Jankowski |
| 7,857,184 B2 | 12/2010 | Viola |
| 7,866,525 B2 | 1/2011 | Scirica |
| 7,866,528 B2 | 1/2011 | Olson et al. |
| 7,871,416 B2 | 1/2011 | Phillips |
| 7,891,531 B1 | 2/2011 | Ward |
| 7,891,533 B2 | 2/2011 | Green et al. |
| 7,913,893 B2 | 3/2011 | Mastri et al. |
| 7,918,869 B2 | 4/2011 | Saadat et al. |
| 7,934,630 B2 | 5/2011 | Shelton, IV et al. |
| 7,955,340 B2 | 6/2011 | Michlitsch et al. |
| 7,959,050 B2 | 6/2011 | Smith et al. |
| 7,963,907 B2 | 6/2011 | Gertner |
| 7,966,799 B2 | 6/2011 | Morgan et al. |
| 7,992,757 B2 | 8/2011 | Wheeler et al. |
| 7,997,469 B2 | 8/2011 | Olson et al. |
| 8,016,176 B2 | 9/2011 | Kasvikis et al. |
| 8,020,741 B2 | 9/2011 | Cole et al. |
| 8,028,884 B2 | 10/2011 | Sniffin et al. |
| 8,033,442 B2 | 10/2011 | Racenet et al. |
| 8,034,077 B2 | 10/2011 | Smith et al. |
| 8,052,697 B2 | 11/2011 | Phillips |
| 8,056,788 B2 | 11/2011 | Mastri et al. |
| 8,061,577 B2 | 11/2011 | Racenet et al. |
| 8,062,236 B2 | 11/2011 | Soltz |
| 8,066,168 B2 | 11/2011 | Vidal et al. |
| 8,070,034 B1 | 12/2011 | Knodel |
| 8,070,036 B1 | 12/2011 | Knodel |
| 8,087,563 B2 | 1/2012 | Milliman et al. |
| 8,091,756 B2 | 1/2012 | Viola |
| 8,096,459 B2 | 1/2012 | Ortiz et al. |
| 8,113,406 B2 | 2/2012 | Holsten et al. |
| 8,132,704 B2 | 3/2012 | Whitman et al. |
| 8,141,762 B2 | 3/2012 | Bedi et al. |
| 8,147,506 B2 | 4/2012 | Ortiz et al. |
| 8,167,186 B2 | 5/2012 | Racenet et al. |
| 8,172,122 B2 | 5/2012 | Kasvikis et al. |
| 8,186,560 B2 | 5/2012 | Hess et al. |
| 8,196,795 B2 | 6/2012 | Moore et al. |
| 8,205,780 B2 | 6/2012 | Sorrentino et al. |
| 8,210,415 B2 | 7/2012 | Ward |
| 8,216,159 B1 | 7/2012 | Leiboff |
| 8,220,690 B2 | 7/2012 | Hess et al. |
| 8,226,602 B2 | 7/2012 | Quijana et al. |
| 8,245,898 B2 | 8/2012 | Smith et al. |
| 8,252,009 B2 | 8/2012 | Weller et al. |
| 8,256,655 B2 | 9/2012 | Sniffin et al. |
| 8,276,801 B2 | 10/2012 | Zemlok et al. |
| 8,292,153 B2 | 10/2012 | Jankowski |
| 8,308,725 B2 | 11/2012 | Bell et al. |
| 8,317,070 B2 | 11/2012 | Hueil et al. |
| 8,322,455 B2 | 12/2012 | Shelton, IV et al. |
| 8,328,061 B2 | 12/2012 | Kasvikis |
| 8,328,064 B2 | 12/2012 | Racenet et al. |
| 8,343,175 B2 | 1/2013 | Ewers et al. |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,436 B2 | 1/2013 | Kasvikis |
| 8,360,297 B2 | 1/2013 | Shelton, IV et al. |
| 8,365,973 B1 | 2/2013 | White et al. |
| 8,365,976 B2 | 2/2013 | Hess et al. |
| 8,382,775 B1 | 2/2013 | Bender et al. |
| 8,393,513 B2 | 3/2013 | Jankowski |
| 8,393,514 B2 | 3/2013 | Shelton, IV et al. |
| 8,403,956 B1 | 3/2013 | Thompson et al. |
| 8,408,442 B2 | 4/2013 | Racenet et al. |
| 8,424,739 B2 | 4/2013 | Racenet et al. |
| 8,439,244 B2 | 5/2013 | Holcolmb et al. |
| 8,439,246 B1 | 5/2013 | Knodel |
| 8,449,560 B2 | 5/2013 | Roth et al. |

(56) References Cited

U.S. PATENT DOCUMENTS

| | | |
|---|---|---|
| 8,453,912 B2 | 6/2013 | Mastri et al. |
| 8,453,914 B2 | 6/2013 | Laurent et al. |
| 8,464,923 B2 | 6/2013 | Shelton, IV |
| 8,465,507 B2 | 6/2013 | Cosgrove et al. |
| 8,469,252 B2 | 6/2013 | Holcomb et al. |
| 8,469,977 B2 | 6/2013 | Balbierz et al. |
| 8,479,969 B2 | 7/2013 | Shelton, IV |
| 8,485,412 B2 | 7/2013 | Shelton, IV et al. |
| 8,496,155 B2 | 7/2013 | Knodel |
| 8,496,156 B2 | 7/2013 | Sniffin et al. |
| 8,499,993 B2 | 8/2013 | Shelton, IV et al. |
| 8,523,041 B2 | 9/2013 | Ishitsuki et al. |
| 8,529,585 B2 | 9/2013 | Jacobs et al. |
| 8,540,128 B2 | 9/2013 | Shelton, IV et al. |
| 8,540,130 B2 | 9/2013 | Moore et al. |
| 8,544,712 B2 | 10/2013 | Jankowski |
| 8,561,872 B2 | 10/2013 | Wheeler et al. |
| 8,573,465 B2 | 11/2013 | Shelton, IV |
| 8,574,243 B2 | 11/2013 | Saadat et al. |
| 8,579,176 B2 | 11/2013 | Smith et al. |
| 8,579,178 B2 | 11/2013 | Holsten et al. |
| 8,590,762 B2 | 11/2013 | Hess et al. |
| 8,596,513 B2 | 12/2013 | Olson et al. |
| 8,608,043 B2 | 12/2013 | Scirica |
| 8,608,046 B2 | 12/2013 | Laurent et al. |
| 8,613,384 B2 | 12/2013 | Pastorelli et al. |
| 8,616,431 B2 | 12/2013 | Timm et al. |
| 8,617,185 B2 | 12/2013 | Bonutti et al. |
| 8,628,544 B2 | 1/2014 | Farascioni |
| 8,628,547 B2 | 1/2014 | Weller et al. |
| 8,647,350 B2 | 2/2014 | Mohan et al. |
| 8,663,245 B2 | 3/2014 | Francischelli et al. |
| 8,668,130 B2 | 3/2014 | Hess et al. |
| 8,672,208 B2 | 3/2014 | Hess et al. |
| 8,672,830 B2 | 3/2014 | Dlugos, Jr. et al. |
| 8,701,958 B2 | 4/2014 | Shelton, IV et al. |
| 8,714,429 B2 | 5/2014 | Demmy |
| 8,720,766 B2 | 5/2014 | Hess et al. |
| 8,727,197 B2 | 5/2014 | Hess et al. |
| 8,727,199 B2 | 5/2014 | Wenchell |
| 8,733,613 B2 | 5/2014 | Huitema et al. |
| 8,740,035 B2 | 6/2014 | Mastri et al. |
| 8,758,392 B2 | 6/2014 | Crainich |
| 8,763,875 B2 | 7/2014 | Morgan et al. |
| 8,800,838 B2 | 8/2014 | Shelton, IV |
| 8,800,840 B2 | 8/2014 | Jankowski |
| 8,801,732 B2 | 8/2014 | Harris et al. |
| 8,808,325 B2 | 8/2014 | Hess et al. |
| 8,840,004 B2 | 9/2014 | Holsten et al. |
| 8,852,218 B2 | 10/2014 | Hughett, Sr. et al. |
| 8,864,009 B2 | 10/2014 | Shelton, IV et al. |
| 8,899,465 B2 | 12/2014 | Shelton, IV et al. |
| 8,925,788 B2 | 1/2015 | Hess et al. |
| 8,945,163 B2 | 2/2015 | Voegele et al. |
| 8,956,390 B2 | 2/2015 | Shah et al. |
| 8,973,804 B2 | 3/2015 | Hess et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,998,058 B2 | 4/2015 | Moore et al. |
| 9,016,541 B2 | 4/2015 | Viola et al. |
| 9,033,203 B2 | 5/2015 | Woodard, Jr. et al. |
| 9,066,721 B2 | 6/2015 | Ichihara et al. |
| 9,084,600 B1 | 7/2015 | Knodel et al. |
| 9,084,601 B2 | 7/2015 | Moore et al. |
| 9,095,339 B2 | 8/2015 | Moore et al. |
| 9,113,862 B2 | 8/2015 | Morgan et al. |
| 9,113,868 B2 | 8/2015 | Felder et al. |
| 9,119,627 B2 | 9/2015 | Cosgrove et al. |
| 9,138,226 B2 | 9/2015 | Racenet et al. |
| 9,149,325 B2 | 10/2015 | Worrell et al. |
| 9,155,528 B2 | 10/2015 | Bender et al. |
| 9,168,039 B1 | 10/2015 | Knodel |
| 9,179,911 B2 | 11/2015 | Morgan et al. |
| 9,180,035 B2 | 11/2015 | Stack et al. |
| 9,216,019 B2 | 12/2015 | Schmid et al. |
| 9,254,131 B2 | 2/2016 | Soltz et al. |
| 9,289,206 B2 | 3/2016 | Hess et al. |
| 9,289,207 B2 | 3/2016 | Shelton, IV |
| 9,307,981 B2 | 4/2016 | Mikkaichi et al. |
| 9,314,362 B2 | 4/2016 | Bender et al. |
| 9,326,768 B2 | 5/2016 | Shelton, IV |
| 9,339,442 B2 | 5/2016 | Tai et al. |
| 9,345,478 B2 | 5/2016 | Knodel |
| 9,364,225 B2 | 6/2016 | Sniffin et al. |
| 9,370,362 B2 | 6/2016 | Petty et al. |
| 9,398,917 B2 | 7/2016 | Whitfield et al. |
| 9,408,604 B2 | 8/2016 | Shelton, IV et al. |
| 9,433,411 B2 | 9/2016 | Racenet et al. |
| 9,439,633 B2 | 9/2016 | O'Dea |
| 9,498,219 B2 | 11/2016 | Moore et al. |
| 9,549,733 B2 | 1/2017 | Knodel |
| 9,561,032 B2 | 2/2017 | Shelton, IV et al. |
| 9,603,595 B2 | 3/2017 | Shelton, IV et al. |
| 9,603,598 B2 | 3/2017 | Shelton, IV et al. |
| 9,615,952 B2 * | 4/2017 | Scott ................ A61B 17/30 |
| 9,636,114 B2 | 5/2017 | Cole et al. |
| 9,675,355 B2 | 6/2017 | Shelton, IV et al. |
| 9,687,233 B2 | 6/2017 | Fernandez et al. |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,724,093 B2 | 8/2017 | Farascioni et al. |
| 9,724,096 B2 | 8/2017 | Thompson et al. |
| 9,730,692 B2 | 8/2017 | Shelton, IV et al. |
| 9,775,613 B2 | 10/2017 | Shelton, IV et al. |
| 9,801,627 B2 | 10/2017 | Harris et al. |
| 9,801,628 B2 | 10/2017 | Harris et al. |
| 9,808,246 B2 | 11/2017 | Shelton, IV et al. |
| 9,808,257 B2 | 11/2017 | Armenteros et al. |
| 9,820,742 B2 | 11/2017 | Covach et al. |
| 9,827,002 B2 | 11/2017 | Hausen et al. |
| 9,844,370 B2 | 12/2017 | Viola et al. |
| 9,848,873 B2 | 12/2017 | Shelton, IV |
| 9,848,875 B2 | 12/2017 | Aronhalt et al. |
| 9,848,878 B2 | 12/2017 | Racenet et al. |
| 9,855,040 B2 | 1/2018 | Kostrzewski |
| 9,861,366 B2 | 1/2018 | Aranyi |
| 9,872,682 B2 | 1/2018 | Hess et al. |
| 9,901,344 B2 | 2/2018 | Moore et al. |
| 9,901,346 B2 | 2/2018 | Moore et al. |
| 9,913,646 B2 | 3/2018 | Shelton, IV |
| 9,924,947 B2 | 3/2018 | Shelton, IV et al. |
| 9,936,953 B2 | 4/2018 | Thompson et al. |
| 9,980,729 B2 | 5/2018 | Moore et al. |
| 9,999,426 B2 | 6/2018 | Moore et al. |
| 9,999,431 B2 | 6/2018 | Shelton, IV et al. |
| 10,004,505 B2 | 6/2018 | Moore et al. |
| 10,045,780 B2 | 8/2018 | Adams et al. |
| 10,085,754 B2 | 10/2018 | Sniffin et al. |
| 10,130,360 B2 | 11/2018 | Olson et al. |
| 10,130,363 B2 | 11/2018 | Huitema et al. |
| 10,172,616 B2 | 1/2019 | Murray et al. |
| 10,194,912 B2 | 2/2019 | Scheib et al. |
| 10,226,250 B2 | 3/2019 | Beckman et al. |
| 10,231,734 B2 | 3/2019 | Thompson et al. |
| 10,238,517 B2 | 3/2019 | Gingras |
| 10,245,032 B2 | 4/2019 | Shelton, IV |
| 10,258,334 B2 | 4/2019 | Adams et al. |
| 10,265,073 B2 | 4/2019 | Scheib et al. |
| 10,278,695 B2 | 5/2019 | Milo |
| 10,278,699 B2 | 5/2019 | Thompson et al. |
| 10,278,707 B2 | 5/2019 | Thompson et al. |
| 10,285,712 B2 | 5/2019 | Cosgrove, III et al. |
| 10,285,837 B1 | 5/2019 | Thompson et al. |
| 10,292,706 B2 | 5/2019 | Jankowski |
| 10,307,161 B2 | 6/2019 | Jankowski |
| 10,307,163 B2 | 6/2019 | Moore et al. |
| 10,314,580 B2 | 6/2019 | Scheib et al. |
| 10,314,589 B2 | 6/2019 | Shelton, IV et al. |
| 10,342,538 B2 | 7/2019 | Racenet et al. |
| 10,383,628 B2 | 8/2019 | Kang et al. |
| 10,390,826 B2 | 8/2019 | Badawi |
| 10,405,856 B2 | 9/2019 | Knodel |

(56) References Cited

U.S. PATENT DOCUMENTS

| | | |
|---|---|---|
| 10,405,860 B2 | 9/2019 | Thompson et al. |
| 10,420,559 B2 | 9/2019 | Marczyk et al. |
| 10,420,560 B2 | 9/2019 | Shelton, IV et al. |
| 10,441,283 B1 | 10/2019 | Thompson et al. |
| 10,456,571 B2 | 10/2019 | Cairns |
| 10,470,911 B2 | 11/2019 | Thompson et al. |
| 10,499,912 B2 | 12/2019 | Scheib et al. |
| 10,537,325 B2 | 1/2020 | Bakos et al. |
| 10,542,986 B2 | 1/2020 | Thompson et al. |
| 10,548,597 B2 | 2/2020 | Dunki-Jacobs et al. |
| 10,624,638 B2 | 4/2020 | Thompson et al. |
| 10,687,807 B2 | 6/2020 | Simms et al. |
| 10,687,810 B2 | 6/2020 | Shelton, IV et al. |
| 10,687,814 B2 | 6/2020 | Dunki-Jacobs et al. |
| 10,716,564 B2 | 7/2020 | Shelton, IV et al. |
| 10,758,231 B2 | 9/2020 | Harris et al. |
| 10,849,623 B2 | 12/2020 | Dunki-Jacobs et al. |
| 10,912,562 B2 | 2/2021 | Dunki-Jacobs et al. |
| 10,966,721 B2 | 4/2021 | Dunki-Jacobs et al. |
| 10,987,108 B2 | 4/2021 | Thompson et al. |
| 2001/0044656 A1 | 11/2001 | Williamson, IV et al. |
| 2002/0143346 A1 | 10/2002 | Mcguckin, Jr. et al. |
| 2003/0125734 A1 | 7/2003 | Mollenauer |
| 2003/0135091 A1 | 7/2003 | Nakazawa et al. |
| 2003/0220660 A1 | 11/2003 | Kortenbach et al. |
| 2004/0006351 A1 | 1/2004 | Gannoe et al. |
| 2004/0006372 A1 | 1/2004 | Racenet et al. |
| 2004/0068267 A1 | 4/2004 | Harvie et al. |
| 2004/0181239 A1 | 9/2004 | Dorn et al. |
| 2005/0006432 A1 | 1/2005 | Racenet et al. |
| 2005/0080444 A1 | 4/2005 | Kraemer |
| 2005/0139633 A1 | 6/2005 | Wukusick et al. |
| 2005/0203547 A1 | 9/2005 | Weller et al. |
| 2006/0011698 A1 | 1/2006 | Okada et al. |
| 2006/0016853 A1 | 1/2006 | Racenet |
| 2006/0020277 A1 | 1/2006 | Gostout et al. |
| 2006/0036267 A1 | 2/2006 | Saadat et al. |
| 2006/0085030 A1 | 4/2006 | Bettuchi et al. |
| 2006/0151568 A1 | 7/2006 | Weller et al. |
| 2006/0229665 A1 | 10/2006 | Wales et al. |
| 2006/0241692 A1 | 10/2006 | McGuckin, Jr. et al. |
| 2007/0023477 A1 | 2/2007 | Whitman et al. |
| 2007/0027469 A1 | 2/2007 | Smith et al. |
| 2007/0029364 A1 | 2/2007 | Kruszynski et al. |
| 2007/0034666 A1 | 2/2007 | Holsten et al. |
| 2007/0034667 A1 | 2/2007 | Holsten et al. |
| 2007/0039997 A1 | 2/2007 | Mather et al. |
| 2007/0056932 A1 | 3/2007 | Whitman et al. |
| 2007/0075114 A1 | 4/2007 | Shelton et al. |
| 2007/0083233 A1 | 4/2007 | Ortiz et al. |
| 2007/0131732 A1 | 6/2007 | Holsten et al. |
| 2007/0179528 A1 | 8/2007 | Soltz et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0213743 A1 | 9/2007 | McGuckin, Jr. |
| 2007/0246505 A1 | 10/2007 | Pace-Floridia et al. |
| 2007/0262116 A1 | 11/2007 | Hueil et al. |
| 2008/0015631 A1 | 1/2008 | Lee et al. |
| 2008/0023522 A1 | 1/2008 | Olson et al. |
| 2008/0033457 A1 | 2/2008 | Francischelli et al. |
| 2008/0035702 A1 | 2/2008 | Holsten et al. |
| 2008/0041918 A1 | 2/2008 | Holsten et al. |
| 2008/0078800 A1 | 4/2008 | Hess et al. |
| 2008/0082124 A1 | 4/2008 | Hess et al. |
| 2008/0087707 A1 | 4/2008 | Jankowski |
| 2008/0097332 A1 | 4/2008 | Greenhalgh et al. |
| 2008/0149684 A1 | 6/2008 | Viola |
| 2008/0164297 A1 | 7/2008 | Holsten et al. |
| 2008/0169329 A1 | 7/2008 | Shelton et al. |
| 2008/0169332 A1 | 7/2008 | Shelton et al. |
| 2008/0190990 A1 | 8/2008 | Holsten et al. |
| 2008/0203134 A1 | 8/2008 | Shah et al. |
| 2008/0249404 A1 | 10/2008 | Mikkaichi et al. |
| 2008/0275480 A1 | 11/2008 | Jacobs et al. |
| 2008/0294179 A1 | 11/2008 | Balbierz et al. |
| 2008/0308602 A1 | 12/2008 | Timm et al. |
| 2009/0001122 A1 | 1/2009 | Prommersberger et al. |
| 2009/0001130 A1 | 1/2009 | Hess et al. |
| 2009/0012556 A1 | 1/2009 | Boudreaux et al. |
| 2009/0020584 A1 | 1/2009 | Soltz et al. |
| 2009/0078739 A1 | 3/2009 | Viola |
| 2009/0134200 A1 | 5/2009 | Farinelli et al. |
| 2009/0173766 A1 | 7/2009 | Wenchell |
| 2009/0209946 A1 | 8/2009 | Swayze et al. |
| 2009/0209986 A1 | 8/2009 | Stewart et al. |
| 2009/0212088 A1 | 8/2009 | Okada et al. |
| 2009/0255974 A1 | 10/2009 | Viola |
| 2009/0261144 A1 | 10/2009 | Sniffin et al. |
| 2009/0308907 A1 | 12/2009 | Nalagatla et al. |
| 2010/0010512 A1 | 1/2010 | Taylor et al. |
| 2010/0072255 A1 | 3/2010 | Olson et al. |
| 2010/0072258 A1 | 3/2010 | Farascioni et al. |
| 2010/0108739 A1 | 5/2010 | Holsten et al. |
| 2010/0114124 A1 | 5/2010 | Kelleher et al. |
| 2010/0121356 A1 | 5/2010 | Hartmann et al. |
| 2010/0137904 A1 | 6/2010 | Wenchell |
| 2010/0145324 A1 | 6/2010 | Nihalani |
| 2010/0213240 A1 | 8/2010 | Kostrzewski |
| 2010/0256634 A1 | 10/2010 | Voegele et al. |
| 2010/0282820 A1 | 11/2010 | Kasvikis |
| 2010/0331866 A1 | 12/2010 | Surti et al. |
| 2011/0004062 A1 | 1/2011 | Asai et al. |
| 2011/0017800 A1 | 1/2011 | Viola |
| 2011/0046653 A1 | 2/2011 | Addington et al. |
| 2011/0071555 A1 | 3/2011 | McBrayer et al. |
| 2011/0084113 A1 | 4/2011 | Bedi et al. |
| 2011/0087279 A1 | 4/2011 | Shah et al. |
| 2011/0152895 A1 | 6/2011 | Nyuli et al. |
| 2011/0160752 A1 | 6/2011 | Aguirre |
| 2011/0178454 A1 | 6/2011 | Gagner et al. |
| 2011/0186614 A1 | 8/2011 | Kasvikis |
| 2011/0190791 A1 | 8/2011 | Jacobs et al. |
| 2011/0208211 A1 | 8/2011 | Whitfield et al. |
| 2011/0226837 A1 | 9/2011 | Baxter, III et al. |
| 2011/0278343 A1 | 11/2011 | Knodel et al. |
| 2011/0290851 A1 | 12/2011 | Shelton, IV |
| 2011/0315739 A1 | 12/2011 | Sniffin et al. |
| 2012/0059400 A1 | 3/2012 | Williamson, IV et al. |
| 2012/0080494 A1 | 4/2012 | Thompson et al. |
| 2012/0123463 A1 | 5/2012 | Jacobs |
| 2012/0175398 A1 | 7/2012 | Sandborn et al. |
| 2012/0203247 A1 | 8/2012 | Shelton, IV et al. |
| 2012/0234899 A1 | 9/2012 | Scheib et al. |
| 2012/0234900 A1 | 9/2012 | Swayze |
| 2012/0248169 A1 | 10/2012 | Widenhouse et al. |
| 2012/0277525 A1 | 11/2012 | O'Dea |
| 2012/0286022 A1 | 11/2012 | Olson et al. |
| 2013/0062394 A1 | 3/2013 | Smith et al. |
| 2013/0075447 A1 | 3/2013 | Weisenburgh, II et al. |
| 2013/0075450 A1 | 3/2013 | Schmid et al. |
| 2013/0092718 A1 | 4/2013 | Soltz et al. |
| 2013/0105549 A1 | 5/2013 | Holsten et al. |
| 2013/0131440 A1 | 5/2013 | Gabriel |
| 2013/0146638 A1 | 6/2013 | Mandakolathur Vasudevan et al. |
| 2013/0146641 A1 | 6/2013 | Shelton, IV et al. |
| 2013/0146642 A1 | 6/2013 | Shelton, IV et al. |
| 2013/0153625 A1 | 6/2013 | Felder et al. |
| 2013/0153634 A1 | 6/2013 | Carter et al. |
| 2013/0153642 A1 | 6/2013 | Felder et al. |
| 2013/0161374 A1 | 6/2013 | Swayze et al. |
| 2013/0165774 A1* | 6/2013 | Nocca .................. A61F 5/0089 600/431 |
| 2013/0172929 A1 | 7/2013 | Hess et al. |
| 2013/0193190 A1 | 8/2013 | Carter et al. |
| 2013/0214025 A1 | 8/2013 | Zemlok et al. |
| 2013/0245652 A1 | 9/2013 | Cosgrove et al. |
| 2013/0256372 A1 | 10/2013 | Baxter, III et al. |
| 2013/0256375 A1 | 10/2013 | Shelton, IV et al. |
| 2013/0256377 A1 | 10/2013 | Schmid et al. |
| 2013/0284791 A1 | 10/2013 | Olson et al. |
| 2013/0306704 A1 | 11/2013 | Balbierz et al. |
| 2013/0327809 A1 | 12/2013 | Shelton, IV et al. |
| 2013/0334288 A1 | 12/2013 | Shelton, IV |

(56) References Cited

U.S. PATENT DOCUMENTS

| | | |
|---|---|---|
| 2013/0341374 A1 | 12/2013 | Shelton, IV et al. |
| 2014/0005678 A1 | 1/2014 | Shelton, IV et al. |
| 2014/0027493 A1 | 1/2014 | Jankowski |
| 2014/0046345 A1 | 2/2014 | Armenteros et al. |
| 2014/0074131 A1 | 3/2014 | Armenteros et al. |
| 2014/0081176 A1 | 3/2014 | Hassan |
| 2014/0082497 A1 | 3/2014 | Chalouhi et al. |
| 2014/0107698 A1 | 4/2014 | Inge |
| 2014/0110457 A1 | 4/2014 | Zhang et al. |
| 2014/0114121 A1 | 4/2014 | Trivedi |
| 2014/0131418 A1 | 5/2014 | Kostrzewski |
| 2014/0131419 A1 | 5/2014 | Bettuchi |
| 2014/0144968 A1 | 5/2014 | Shelton, IV |
| 2014/0148731 A1 | 5/2014 | Radi et al. |
| 2014/0171744 A1 | 6/2014 | Racenet et al. |
| 2014/0183242 A1 | 7/2014 | Farascioni et al. |
| 2014/0184519 A1 | 7/2014 | Benchenaa et al. |
| 2014/0191015 A1 | 7/2014 | Shelton, IV |
| 2014/0214025 A1 | 7/2014 | Worrell et al. |
| 2014/0231489 A1 | 8/2014 | Balbierz et al. |
| 2014/0239037 A1 | 8/2014 | Boudreaux et al. |
| 2014/0257353 A1 | 9/2014 | Whitman et al. |
| 2014/0263570 A1 | 9/2014 | Hopkins et al. |
| 2014/0276932 A1 | 9/2014 | Williams et al. |
| 2014/0291379 A1 | 10/2014 | Schellin et al. |
| 2015/0048141 A1 | 2/2015 | Felder et al. |
| 2015/0083780 A1 | 3/2015 | Shelton, IV et al. |
| 2015/0133740 A1 | 5/2015 | Dierking et al. |
| 2015/0157318 A1 | 6/2015 | Beardsley et al. |
| 2015/0173755 A1 | 6/2015 | Baxter, III et al. |
| 2015/0173762 A1 | 6/2015 | Shelton, IV et al. |
| 2015/0209034 A1 | 7/2015 | Viola et al. |
| 2015/0265276 A1 | 9/2015 | Huitema et al. |
| 2015/0297224 A1 | 10/2015 | Hall et al. |
| 2015/0297227 A1 | 10/2015 | Huitema et al. |
| 2015/0320423 A1 | 11/2015 | Aranyi |
| 2015/0351764 A1 | 12/2015 | Shelton, IV |
| 2016/0058447 A1 | 3/2016 | Posada et al. |
| 2016/0058594 A1 | 3/2016 | Armenteros et al. |
| 2016/0066916 A1 | 3/2016 | Overmyer et al. |
| 2016/0067074 A1 | 3/2016 | Thompson et al. |
| 2016/0089148 A1 | 3/2016 | Harris et al. |
| 2016/0166256 A1 | 6/2016 | Baxter, III et al. |
| 2016/0183945 A1 | 6/2016 | Shelton, IV et al. |
| 2016/0199061 A1 | 7/2016 | Shelton, IV et al. |
| 2016/0199088 A1 | 7/2016 | Shelton, IV et al. |
| 2016/0213302 A1 | 7/2016 | Frushour |
| 2016/0235409 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242783 A1 | 8/2016 | Shelton, IV et al. |
| 2016/0262744 A1 | 9/2016 | Milo et al. |
| 2016/0262750 A1 | 9/2016 | Hausen et al. |
| 2016/0262921 A1 | 9/2016 | Balbierz et al. |
| 2016/0270792 A1 | 9/2016 | Sniffin et al. |
| 2016/0324527 A1 | 11/2016 | Thompson et al. |
| 2016/0354085 A1 | 12/2016 | Shelton, IV et al. |
| 2016/0367250 A1 | 12/2016 | Racenet et al. |
| 2017/0007248 A1 | 1/2017 | Shelton, IV et al. |
| 2017/0014125 A1 | 1/2017 | Shelton, IV et al. |
| 2017/0055991 A1 | 3/2017 | Kang |
| 2017/0086847 A1 | 3/2017 | DiNardo et al. |
| 2017/0095251 A1 | 4/2017 | Thompson et al. |
| 2017/0105728 A1 | 4/2017 | Scheib et al. |
| 2017/0172571 A1 | 6/2017 | Thompson et al. |
| 2017/0231633 A1 | 8/2017 | Marczyk et al. |
| 2017/0290588 A1 | 10/2017 | Thompson et al. |
| 2017/0303952 A1 | 10/2017 | Nativ et al. |
| 2017/0319210 A1 | 11/2017 | Moore et al. |
| 2017/0333041 A1 | 11/2017 | Moore et al. |
| 2017/0360447 A1 | 12/2017 | Armenteros et al. |
| 2017/0367697 A1 | 12/2017 | Shelton, IV et al. |
| 2018/0014826 A1 | 1/2018 | Scheib et al. |
| 2018/0036000 A1 | 2/2018 | Terada et al. |
| 2018/0036005 A1 | 2/2018 | Covach et al. |
| 2018/0092641 A1 | 4/2018 | Aranyi |
| 2018/0168620 A1 | 6/2018 | Huang et al. |
| 2018/0168633 A1 | 6/2018 | Shelton, IV et al. |
| 2018/0199939 A1 | 7/2018 | Thompson et al. |
| 2018/0199941 A1 | 7/2018 | Thompson et al. |
| 2018/0235625 A1 | 8/2018 | Shelton, IV et al. |
| 2018/0235626 A1 | 8/2018 | Shelton, IV et al. |
| 2018/0280020 A1 | 10/2018 | Hess et al. |
| 2018/0317905 A1 | 11/2018 | Olson et al. |
| 2019/0000455 A1 | 1/2019 | Adams et al. |
| 2019/0046186 A1 | 2/2019 | Dunki-Jacobs et al. |
| 2019/0046189 A1 | 2/2019 | Dunki-Jacobs et al. |
| 2019/0046190 A1 | 2/2019 | Dunki-Jacobs et al. |
| 2019/0046191 A1 | 2/2019 | Dunki-Jacobs et al. |
| 2019/0046192 A1 | 2/2019 | Dunki-Jacobs et al. |
| 2019/0046193 A1 | 2/2019 | Dunki-Jacobs et al. |
| 2019/0105042 A1 | 4/2019 | Huitema et al. |
| 2019/0133577 A1 | 5/2019 | Weadock et al. |
| 2019/0150924 A1 | 5/2019 | Thompson et al. |
| 2019/0209173 A1 | 7/2019 | Thompson et al. |
| 2019/0209175 A1 | 7/2019 | Thompson et al. |
| 2019/0261985 A1 | 8/2019 | Adams et al. |
| 2019/0261991 A1 | 8/2019 | Beckman et al. |
| 2019/0269408 A1 | 9/2019 | Jankowski |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0307450 A1 | 10/2019 | Thompson et al. |
| 2019/0343519 A1 | 11/2019 | Thompson et al. |
| 2019/0380742 A1 | 12/2019 | Hall et al. |
| 2019/0388092 A1 | 12/2019 | Thompson et al. |
| 2020/0008964 A1 | 1/2020 | Thompson et al. |
| 2020/0015822 A1 | 1/2020 | Marczyk et al. |
| 2020/0054326 A1 | 2/2020 | Harris et al. |
| 2020/0100790 A1 | 4/2020 | DiNardo et al. |
| 2020/0205810 A1 | 7/2020 | Posey et al. |
| 2020/0205827 A1 | 7/2020 | Bakos et al. |
| 2020/0214703 A1 | 7/2020 | Thompson et al. |
| 2020/0229818 A1 | 7/2020 | Thompson et al. |
| 2020/0268385 A1 | 8/2020 | Dunki-Jacobs et al. |
| 2020/0297344 A1 | 9/2020 | Dunki-Jacobs et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305873 A1 | 10/2020 | Dunki-Jacobs et al. |
| 2020/0390443 A1 | 12/2020 | Thompson et al. |
| 2021/0128335 A1 | 5/2021 | Thompson et al. |

FOREIGN PATENT DOCUMENTS

| | | |
|---|---|---|
| EP | 399699 A1 | 11/1990 |
| EP | 503662 A1 | 9/1992 |
| EP | 0666057 A2 | 8/1995 |
| EP | 669104 A1 | 8/1995 |
| EP | 0399699 B1 | 11/1995 |
| EP | 0503662 B1 | 6/1997 |
| EP | 1090592 A1 | 4/2001 |
| EP | 1616526 A1 | 1/2006 |
| EP | 1769766 A1 | 4/2007 |
| EP | 1774916 A1 | 4/2007 |
| EP | 1806101 A1 | 7/2007 |
| EP | 1875868 A1 | 1/2008 |
| EP | 1875870 A1 | 1/2008 |
| EP | 1938759 A2 | 7/2008 |
| EP | 2005896 A2 | 12/2008 |
| EP | 2005897 A2 | 12/2008 |
| EP | 2005898 A2 | 12/2008 |
| EP | 2005899 A2 | 12/2008 |
| EP | 2005900 A2 | 12/2008 |
| EP | 2005901 A1 | 12/2008 |
| EP | 1774916 B1 | 2/2009 |
| EP | 2019633 A1 | 2/2009 |
| EP | 2090247 A1 | 8/2009 |
| EP | 2111803 A2 | 10/2009 |
| EP | 2245993 A2 | 11/2010 |
| EP | 2319424 A1 | 5/2011 |
| EP | 2382928 A1 | 11/2011 |

(56) References Cited

FOREIGN PATENT DOCUMENTS

| | | |
|---|---|---|
| EP | 2019633 B1 | 8/2012 |
| FR | 2731895 A1 | 9/1996 |
| GB | 2298905 A | 9/1996 |
| WO | 01/54594 A1 | 8/2001 |
| WO | 03/094747 A1 | 11/2003 |
| WO | 2007/009099 A2 | 1/2007 |
| WO | 2007019268 A2 | 2/2007 |
| WO | 2007102152 A2 | 9/2007 |
| WO | 2008/042022 A1 | 4/2008 |
| WO | 2008039238 A1 | 4/2008 |
| WO | 2008039249 A1 | 4/2008 |
| WO | 2008039250 A1 | 4/2008 |
| WO | 2008039270 A1 | 4/2008 |
| WO | 2008042021 A1 | 4/2008 |
| WO | 2008042043 A1 | 4/2008 |
| WO | 2008042044 A2 | 4/2008 |
| WO | 2008042045 A2 | 4/2008 |
| WO | 2008094210 A1 | 8/2008 |
| WO | 2008141288 A1 | 11/2008 |
| WO | 2009038550 A1 | 3/2009 |
| WO | 2010/011661 A1 | 1/2010 |
| WO | 2011/044032 A3 | 4/2011 |
| WO | 2011044032 A2 | 4/2011 |
| WO | 2011094700 A1 | 8/2011 |
| WO | 2012/141679 A1 | 10/2012 |
| WO | 2013/151888 A1 | 10/2013 |
| WO | 2014026170 A2 | 2/2014 |
| WO | 2014/085099 A1 | 6/2014 |
| WO | 2015063609 A2 | 5/2015 |
| WO | 2015153324 A1 | 10/2015 |
| WO | 2015153340 A2 | 10/2015 |
| WO | 2016033221 A1 | 3/2016 |

OTHER PUBLICATIONS

Parikh, M.D. et al., Surgical Strategies That May Decrease Leak After Laparoscopic Sleeve Gastrectomy, 257 Annals of Surgery 231, Feb. 2013; 7 pages.
Aladar de Petz, M.D., Aseptic Technic of Stomach Resections, 86 Annals of Surgery 388, Sep. 1927; 5 pages.
John D. Harrah, M.D., A Lung Clamp for Use with Mechanical Staplers, 28 The Annals of Thoracic Surgery 489, Nov. 1979; 2 pages.
Bram D. Zuckerman, M.D., Food and Drug Administration, Letter to AtriCure, Inc. Addressing Indication For Use of AtriClip LAA Exclusion System w/Pre-loaded Gillnov-Cosgrove Clip, Jun. 10, 2010; 3 pages.
510(k) Summary for AtriClip LAA Exclusion System with preloaded Gillinov-Cosgrove Clip, published Jun. 10, 2010; 6 pages.
CMS Description of Open Left Atrial Appendage Occlusion with "U" Fastener Implant; 1 page.
510(k) Summary for TigerPaw(R) System, published Oct. 29, 2010; 6 pages.
Pfiedler Enterprises, Science of Stapling: Urban Legend and Fact, Published Jun. 4, 2012; 38 pages.
Written Opinion of the Int'l Searching Authority and International Search Report for PCT/US2015/048740 dated as dated Feb. 17, 2016; 12 pages.
Written Opinion of the Int'l Searching Authority and International Search Report for PCT/US2015/022990 dated as dated Sep. 30, 2015; 10 pages.
Written Opinion of the Int'l Searching Authority and International Search Report for PCT/US2015/022904 dated as dated Jun. 25, 2015; 6 pages.
Search Report and Written Opinion of the International Searching Authority for International Patent App. No. PCT/US2014/070869 dated as dated Apr. 21, 2015; 17 pages.
Supplementary Partial European Search Report of the European Patent Office, Issued in European Application No. 14872137; dated Dec. 12, 2016; 5 pages.
Supplementary European Search Report of the European Patent Office, Issued in European Application No. 15772561.5-1664; dated Mar. 15, 2017; 8 pages.
International Preliminary Report on Patentability and Written Opinion of the International Searching Authority in Application No. PCT/US2015/048740 dated as dated Mar. 7, 2017; 8 pages.
Supplementary European Search Report of the European Patent Office, Issued in European Application No. 14872137.6-1664/3082620; dated Mar. 28, 2017; 15 pages.
European Search Report of the European Patent Office, Issued in European Application No. 15774247.9-1654; dated Dec. 23, 2016; 11 pages.
Australian Examination Report in Application No. 2016208416; dated May 18, 2017; 4 pages.
International Preliminary Report on Patentability and Written Opinion of the International Searching Authority received in Application No. PCT/US2018/046743; dated Feb. 18, 2020; 17 pages.
Australian Examination Report in Application No. 2015241267; dated Feb. 25, 2019; 6 pages.
Felicien M. Steichen and Mark M. Ravitch, Stapling in Surgery, Figure 1-11C, Year Book Medical Publishers, Inc. 1984; 3 pages.
M Jacobs et al., Laparoscopic sleeve gastrectomy: a retrospective review of 1- and 2-year results, Surg Endosc. Apr. 2010;24(4):781-5. doi: 10.1007/S00464-009-0619-8. Epub Aug. 19, 2009; abstract only; 2 pages.
JP Regan et al., Early experience with two-stage laparoscopic Roux-en-Y gastric bypass as an alternative in the super-super obese patient, Obes Surg. Dec. 2003;13(6):861-4; abstract only; 2 pages.
Australian Examination Report in Application No. 2018203527; dated Oct. 22, 2018; 5 pages.
International Search Report and Written Opinion of the International Searching Authority for International Patent App. No. PCT/US2018/046743 dated as dated Dec. 4, 2018; 20 pages.
Australian Examination Report in Application No. 2015241193; dated Dec. 11, 2018; 5 pages.
Examination Report of the European Patent Office, Issued in European Application No. 15772561.5-1122; dated Oct. 29, 2018; 7 pages.
Search Report of the State Intellectual Property Office of the People's Republic of China, Issued in Chinese Application No. 201480075706.2; dated Nov. 28, 2018; 3 pages.

* cited by examiner

SYSTEMS AND METHODS FOR MEASURING VOLUME OF POTENTIAL SLEEVE IN A SLEEVE GASTRECTOMY

REFERENCE TO RELATED APPLICATION

This application is a continuation application of U.S. non-provisional application Ser. No. 15/267,414, filed Sep. 16, 2016, which claims priority to U.S. Provisional Patent Application No. 62/219,564, filed Sep. 16, 2015, which are hereby incorporated by reference in their entirety.

BACKGROUND

Obesity is a disease that affects a significant portion of the world's population and leads to multiple chronic medical conditions and premature death from cardiovascular events and cancer. In particular, the United States has a current, and worsening obesity epidemic. The U.S. Centers for Disease Control and Prevention (CDC) reports that over 33% of the U.S. population is obese, with a Body Mass Index (BMI) of over 30, and another 35-40% of the US population is overweight, with a BMI of 25-30. The CDC reports that the percent of the US population being either overweight or obese by 2018 will be 75%. The CDC also reports that obesity directly costs the U.S. economy $147 billion currently, and projects that the costs will approach $315 billion by 2020.

Further, obesity has environmental, genetic and behavioral origins but is intractable to most medical and behavioral interventions. To help reduce obesity and/or facilitate weight loss, bariatric surgery may be an option for some patients that may be overweight. Typically, bariatric surgery may be an effective long-term treatment option for patients with a BMI greater than 35. Despite the 20 million patients who are eligible for weight loss surgery in the U.S., the number of procedures per year has plateaued at about 200 thousand, eliminating any public health effect of surgery.

In recent years, a popular form of bariatric surgery may include a laparoscopic vertical sleeve gastrectomy (e.g., which may remove approximately 80% of the stomach). Laparoscopic vertical sleeve gastrectomy may be a procedure that may be safer and more effective for patients eligible for weight loss surgery. In fact, it has been accepted as the surgery that should be offered to most morbidly obese patients over, for example, laparoscopic adjustable gastric banding and laparoscopic Roux-en-Y gastric bypass. As such, the surgery has been adopted by bariatric surgeons and is now the most commonly performed weight loss surgery.

Vertical sleeve gastrectomy is typically performed using standard laparoscopic equipment. The greater curvature of the stomach is mobilized using vessel-sealing devices, sealing the gastric branches of the gastroepiploic vessels and the short gastric vessels. The posterior adhesions of the stomach are also divided so the stomach is fully mobilized while the blood supply to the lesser curvature remains intact.

Following mobilization of the stomach a calibration tube is typically introduced into the stomach through the mouth. Resection is accomplished by applying a series of staples from a laparoscopic linear surgical stapler, for example, along the calibration tube in a staple line. The staple line may be important in sleeve gastrectomy as the amount of weight lost and complications or consequences may be a direct result of the quality of the resultant sleeve gastrectomy pouch formed from the staple line (e.g., the portion of the stomach not rescinded by the staple line). The complications or consequences may include gastroesophageal reflux disorder (GERD), weight loss failure or weight regain, food intolerance, staple line bleed, leak, and/or the like.

To perform the sleeve gastrectomy and produce sleeve gastrectomy pouch (e.g., from the staple line), a sleeve gastrectomy stapling guide and a catheter or tube may be used. Although the combination of the stapling guide and catheter or tube may help produce a better staple line, a surgeon may still need to estimate or envision an adequate distance to form the sleeve gastrectomy pouch with a suitable volume, shape, and/or size. To help improve the volume, size and/or shape of the sleeve gastrectomy pouch, the surgeon may want to measure volume of the sleeve gastrectomy pouch prior to stapling. Unfortunately, currently, the volume may be measured in follow ups after the sleeve gastrectomy may have been performed to diagnose problems that may have occurred and/or determine why the sleeve gastrectomy may not have been successful. Further, other surgical weight loss procedures such as vertical banded gastroplasty that may provide techniques and/or devices to measure volume of a pouch prior to placing a band at the area of the stomach the surgeon wishes to remove as part of the pouch may not be suitable for use in a sleeve gastrectomy. For example, those current techniques may not provide a stapling guide that may be long enough to occlude the length necessary to produce the staple line in a sleeve gastrectomy and also may not provide devices and/or techniques to occlude the esophagus and the pylorus to pressure the sleeve gastrectomy pouch necessary to measure its volume.

SUMMARY

In an example herein, one or more medical devices may be provided that may be used, for example, in bariatric surgery including a vertical sleeve gastrectomy. The one or more medical devices may include a laparoscopic sleeve gastrectomy stapling guide in conjunction with a catheter or tube in accordance with one or more examples. According to an example, occlusion devices may be integrated with the catheter or tube or separate therefrom to occlude one or more proximal or distal landmarks of a stomach and the stapling guide may be used to occlude a lateral boundary of the stomach. The area defined within the occluded portions and lateral boundary may be a potential resultant sleeve of the sleeve gastrectomy. A volume of the potential resultant sleeve may be determined by inserting fluid or gas into the catheter or tube, measuring pressure, and/or calculating the volume therefrom. In an example, the volume of the sleeve may indicate whether a surgeon may need to make the potential resultant sleeve larger or smaller (e.g., by moving the stapling guide or stapler) prior to stapling.

DETAILED DESCRIPTION

As described herein, systems and/or methods may be provided for performing a sleeve gastrectomy. For example, a medical device may be provided that may include a first medical device and a second medical device. The first medical device may be positioned in an interior of the stomach. The first medical device may be a catheter or medical tube. The first medical device may be positioned, for example, by inserting the first medical device into a mouth of a patient to access the interior of the stomach. In an example, the first medical device may include one or more portions that may occlude landmarks of a stomach such as a pylorus and/or landmarks that may provide access to the stomach such as an esophagus. In an additional or alternative example, one or more additional medical devices that may not be integrated into the first medical device may be used in conjunction with the first medical device to occlude such landmarks. These additional devices may be exterior to the stomach according to one example. According to one or more examples, the first medical device may allow or enable fluid to pass through it into the stomach.

Further, in one example, the second medical device such as a clamp or stapler may be positioned on an exterior of the stomach such that the second medical device may be configured to demonstrate or create a path such as a resection line or staple line along the stomach at which the sleeve gastrectomy may be performed. In one example, the second medical device may be positioned on the exterior of the stomach relative to the first medical device (e.g., adjacent to, near, in proximity to, and/or the like). In such an example, the first medical device may be used as a reference to position the second medical device. The second medical device may slide or move along the exterior of the stomach prior to stapling based on a sleeve volume that may be measured for a resultant sleeve.

Figure 1:
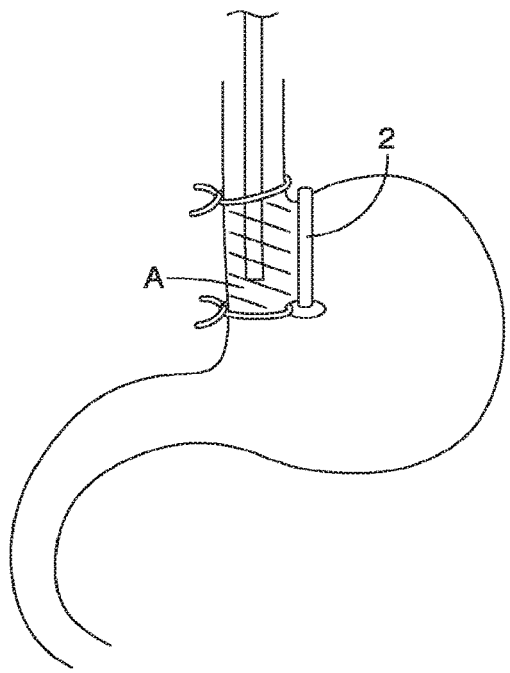
FIG. 1 depicts a front view of an example volume of a portion of a stomach that may be measured in a banded gastroplasty in one or more examples.
Figure 2:
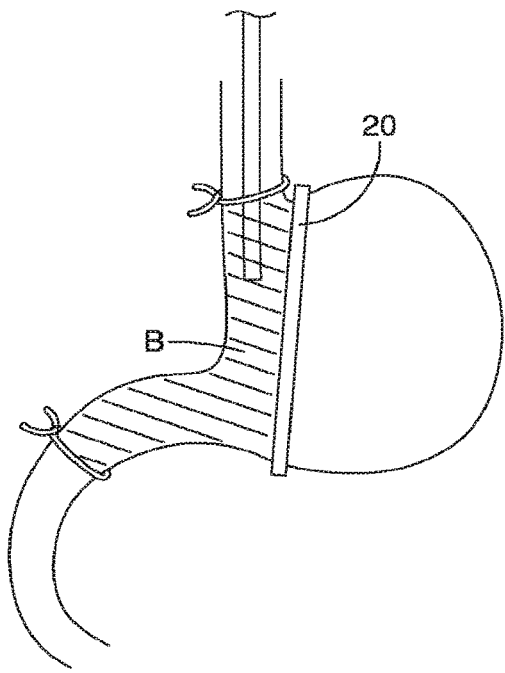
FIG. 2 depicts a front view of an example volume of a potential resultant sleeve that may be measured in a sleeve gastrectomy in one or more examples.

As described herein, in one or more examples, the first medical device in conjunction or combination with the second medical device and/or the one or more additional devices may be used to measure a volume of a potential resultant sleeve that may be formed thereby. FIG. 2 illustrates an example volume of a potential resultant sleeve that may be measured. As shown in FIG. 2, a volume of area B may be measured in one or more examples herein for a potential resultant sleeve in a sleeve gastrectomy. The area B may be larger for a resultant sleeve in a sleeve gastrectomy than an area A shown in FIG. 1 that may be provided in a banded gastroplasty and in which a volume may be measured. Further, as described herein, a guide 2 that may be used in the banded gastroplasty may not be long enough (e.g., as compared to a second medical device 20) to occlude the length of the stomach to produce the staple line in a sleeve gastrectomy and also may not provide devices and/or techniques (e.g., first and second occlusion devices) to occlude the first landmark and the second landmark (e.g., the pylorus and esophagus at the GEJ or GE junction) to pressurize the potential resultant sleeve in a sleeve gastrectomy at a level necessary to measure its volume as shown in FIGS. 1 and 2.

In an example (e.g., upon reaching a suitable volume or desired volume), the sleeve gastrectomy (e.g., resection of part of the stomach) may be performed along the path produced by the second medical device. For example, the surgeon may fully engage the second medical device and may resect the stomach along the path to produce the resected resultant sleeve or permanent resultant upon reaching a suitable volume that may produce a resected or permanent resultant sleeve of the stomach. For example, a resection or staple line may be created (e.g., using a surgical stapler) along the path (e.g., staple line or resection line) thereby producing the resected or permanent resultant sleeve. In one or more examples herein, the resultant sleeve of the stomach that may be created by the path (e.g., the resection or staple line) may include a diameter of approximately 1 to 3 cm near the first landmark (e.g., the IA), approximately 2 to 6 cm near a second landmark (e.g., a pylorus) of the stomach, and approximately 0 to 2 cm near a third landmark (e.g., a gastroesophageal junction (GEJ) or GE junction) of the stomach.

Figure 3:
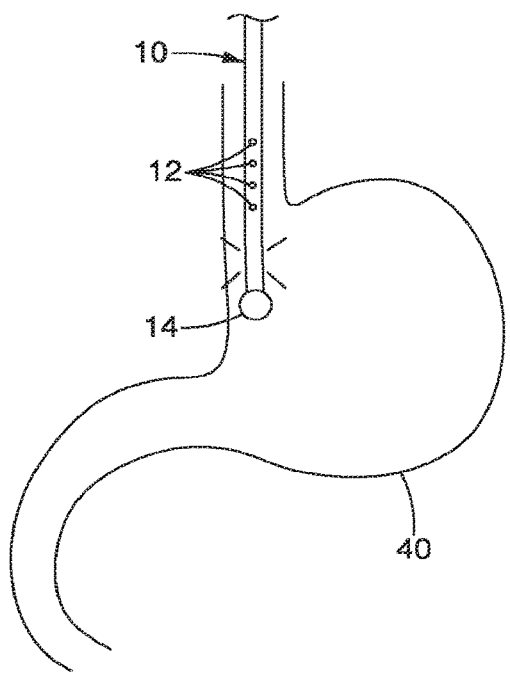
FIG. 3 depicts a front view of a stomach shown with an inserted first medical device having a first occlusion portion has been inserted according to one embodiment.
Figure 4:
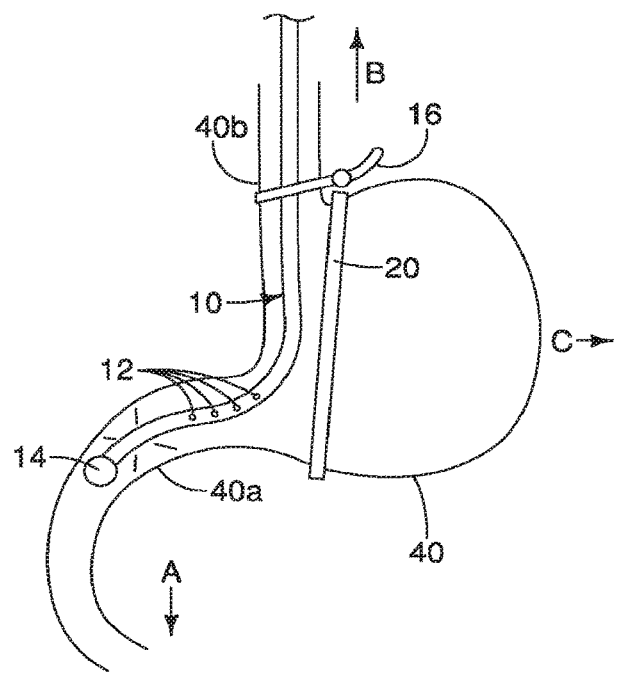
FIG. 4 depicts a front view of a stomach with the inserted first medical device shown in FIG. 3 in cooperation with a second occlusion device according to one embodiment.
Figure 5:
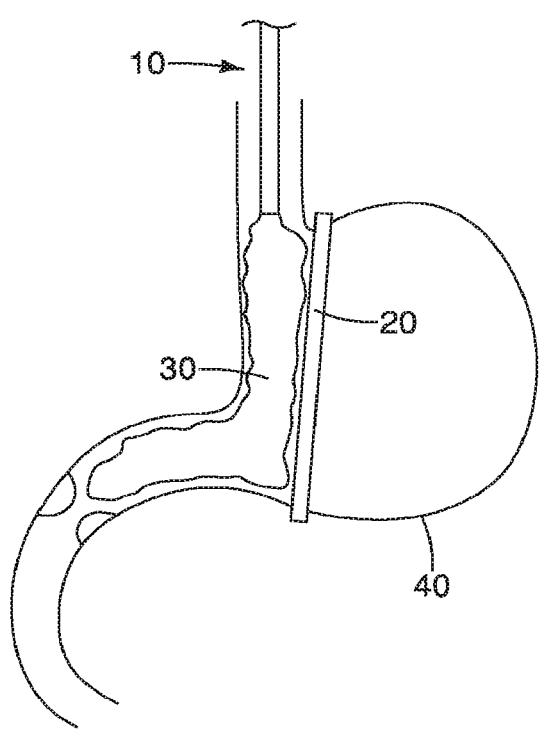
FIG. 5 depicts a front view of a stomach shown with a sleeve volume measurement system having a compliant balloon associated with one embodiment.
Figure 6:
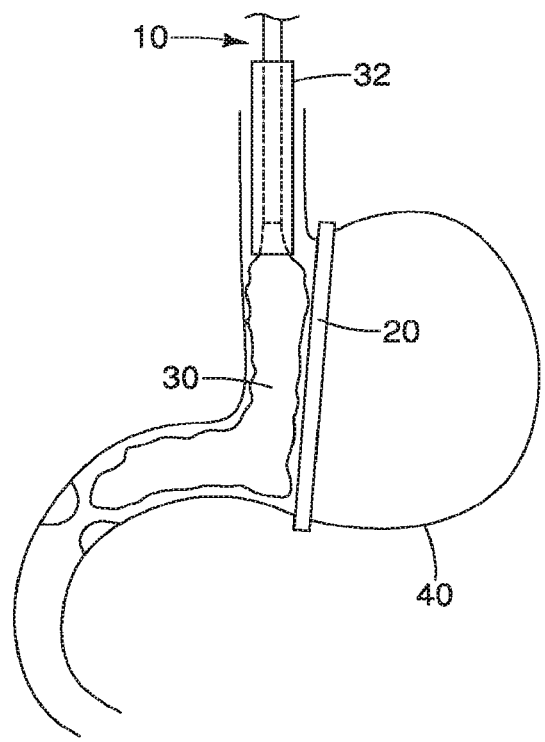
FIG. 6 depicts a front view of a stomach with the compliant balloon of FIG. 5 shown with an associated sheath according to one embodiment.

FIGS. 3-4 depict an example method or procedure and devices associated therewith that may be used to measure sleeve volume in one or more examples. As shown, a first medical device 10 may be inserted into a stomach 40 through a mouth and positioned along a lesser curve (e.g., the IA) of the stomach 40. The first medical device 10 may be a catheter or an elongated tube such as an orogastric tube that may be hollow or partially hollow in examples. Further, in examples, the first medical device 10 may include a plurality of catheters or elongated tubes that may be housed within each other (not shown). The first medical device 10 may include one or more ports (not shown) at a proximal end thereof and one or more apertures or openings 12 at a distal end thereof. The ports may be on the exterior of the stomach 40 and may receive fluid or gas that may be passed through the first medical device 10 until it reaches the apertures or holes 12. The fluid or gas may pass through the apertures and holes 12 into the interior of the stomach 40. As described herein, the fluid or gas may be received and pass through the first medical device 10 into the stomach 40 such that a pressure may be measured and a volume calculated for a potential resultant sleeve.

In an example, the first medical device 10 may include a first occlusion device 14. In an example, the first occlusion device 14 may be positioned past a landmark 40*a* such as a pylorus of the stomach 40 such that when positioned past the landmark 40*a* the first occlusion portion 40 may occlude fluid or gas from passing or flowing beyond the landmark 40*a* in direction A. As shown, the first occlusion device 14 may be a balloon on the distal end of the first medical device 10 that may be inflated to occlude the landmark 40*a*. As such, in an example, the first occlusion device 14 may be integrated into the first medical device 10.

According to an additional or alternative example, the first occlusion device 14 may include another medical device such as clamp, penrose, band, and/or the like that may be used to occlude the landmark 40*a*. For example, the first occlusion portion 14 may be a separate medical device (e.g., from the first medical device 10) that may be positioned at the landmark 40*a* (e.g., on an exterior of the stomach 40 or wrapped therearound) to occlude fluid or gas from passing beyond the landmark 40*a* in direction A.

In an example, a second occlusion device 16 may be provided. The second occlusion device 16 may be positioned at a landmark 40*b* such as a GE junction or GEJ of the stomach 40 and wrapped around, for example, the esophagus to occlude fluid or gas from passing beyond the landmark 40*b* in direction B. The second occlusion device 15 may be a clamp, penrose or elastomeric band that may be positioned at the landmark 40*b* and wrapped around the esophagus to prevent fluid or gas from passing therebeyond.

According to an additional or alternative example (not shown in FIGS. 3-4, but shown, for example, in FIG. 12), the second occlusion device 16 may be integrated into the first medical device 10 and adjusted to be positioned at the landmark 40*b* as described herein.

As shown, a second medical device 20 may be provided. The second medical device 20 may be positioned on an exterior of the stomach 40. The second medical device may be a clamp, a single cartridge sleeve gastrecomty stapler, and/or the like. The second medical device 20 may span a length of a potential staple line or resection line of the stomach 40 undergoing the sleeve gastrectomy such that it may be configured to demonstrate or create a path such as a resection line or staple line along the stomach 40 at which the sleeve gastrectomy may be performed. In one example, the second medical device 20 may be positioned on the exterior of the stomach relative to the first medical device (e.g., adjacent to, near, in proximity to, and/or the like). In such an example, the first medical device 10 may be used as a reference to position the second medical device 20. The second medical device 20 may slide or move along the exterior of the stomach prior to stapling based on a sleeve volume that may be measured for a potential resultant sleeve. The second medical device 20 may also not enable fluid or gas to pass beyond laterally in direction C and in conjunction with the first medical occlusion device 12 and second occlusion device 16 may define a potential resultant sleeve that may fluid and gas may be trapped within to measure volume as described herein.

According to examples, the second medical device 20 may be a clamp or stapler that may be adjusted or at least partially closed or fully closed by adjusting resistance of a cable thereof (not shown) in a loop cable assembly included therein (not shown). In such an example, resistance may be provided by springs (not shown) that resist the cable being pulled. The spring constant may be different in the proximal and the distal end of the second medical device 20 and, thus, one end may be pulled down before the other such that the stomach may be manipulated at different points or part. Additionally, in examples, the second medical device 20 may have different traction surfaces along the length thereof such that different points or parts of the stomach may be manipulated without allowing movement of other points or parts (e.g., different parts of the stomach may be clamped while others may not be). The second medical device 20 may further be wider along portions thereof (e.g., may have a non-uniform width). For example, the second medical device 20 may be wider along a portion that may be positioned near a landmark such as an IA of the stomach 40.

As shown, in performing the sleeve gastrectomy (e.g., a method or procedure thereof), the first medical device 10 may be inserted into the stomach 40 and adjusted proximally and distally such that first occlusion device 14 may be positioned at the landmark 40*a* (e.g., near or around the pylorus). As shown, the second occlusion device 16 may be positioned at the landmark 40*b*. The first occlusion device 14 may be inflated to occlude fluid or gas from passing in direction A beyond the landmark 40*a*. For example, the first medical device 10 may be positioned along the lesser curve of the stomach 40 with the first occlusion device 12 beyond or past the landmark 40*a* (e.g., the pylorus). The first occlusion device 12 may be inflated and withdrawn to withstand pressure (for example, 70 cm H20) and to enable gas to be trapped in a potential resultant sleeve (i.e., not allow gas to pass beyond the landmark 40*a* or the occlusion point produced thereby). The second occlusion device 16 may be wrapped or secured around the landmark 40*b* as shown in an example to occlude fluid or gas from passing in direction B beyond landmark 40*b*.

The second medical device 20 may be positioned on the exterior of the stomach 40 (e.g., as shown) at a location a surgeon may desire or may believe produces a resultant sleeve with a desired shape, size, and/or volume. According to an example (e.g., after positioning the second medical device 20 at the desired location), the second medical device 20 may be at least partially closed thereby forming a potential resection line and a potential resultant sleeve formed thereby. As described herein, the first occlusion device 14 of the first medical device 10, second occlusion device 16, and second medical device 20 may define a potential resultant sleeve and may prevent gas or fluid from escaping such a sleeve when determining a volume thereof.

In an example (e.g., upon occluding at the landmarks 40*a*, 40*b* and positioning the second medical device 20), an amount (e.g., a predetermined or predefined amount) of fluid such as water, saline solution, and/or the like or gas may be inserted into the first medical device 10 at a proximal end thereof (e.g., via the port not shown) and may pass therethrough out of the apertures or openings 12 and into the portion of the stomach 40 defined by the area created by the first and second occlusion devices 14, 16 at the landmarks 40*a*, 40*b* respectively and and the path along the second medical device 20. In an example, the amount of fluid or gas may be between from about 20 ml to about 200 ml.

Pressure may be measured (e.g., using a pressure measurement device not shown) and a volume of the potential resultant sleeve defined by the landmarks 40a, 40b and second medical device may be calculated based on the amount of fluid or gas used and the pressure measured therefrom.

According to an example, the volume may be used to determine whether the potential resultant sleeve may be suitable for resection and/or may provide a desired resected or permanent resultant sleeve size, shape, and/or the like. For example, if based on the measurement and/or calculation, the volume may be too low to provide a resected resultant sleeve desired by a surgeon, the second medical device 20 may be moved laterally along the exterior surface away from the landmarks 40a, 40b and/or the IA such that the potential resultant sleeve may become larger. Likewise, in an example, if based on the measurement and/or calculated, the volume may be too high to provide a resected resultant sleeve desired by a surgeon, the second medical device 20 may be moved medially along the exterior of the stomach toward the landmarks 40a, 40b and/or the IA of the stomach 40 such that the potential resultant sleeve may become smaller. The pressure may be re-measured in response to moving the second medical device 20 to determine whether subsequent medial or lateral movements as described herein may be needed thereto to achieve a desired resected or permanent resultant sleeve.

In an example (e.g., upon reaching a suitable volume or desired volume), the sleeve gastrectomy (e.g., resection of part of the stomach 40) may be performed along the path produced by the second medical device. For example, the surgeon may fully engage the second medical device 20 and may resect the stomach along the path to produce the resected resultant sleeve or permanent resultant upon reaching a suitable volume that may produce a resected or permanent resultant sleeve of the stomach. For example, a resection or staple line may be created (e.g., using a surgical stapler) along the path (e.g., staple line or resection line) thereby producing the resected or permanent resultant sleeve. In one or more examples herein, the resultant sleeve of the stomach that may be created by the path (e.g., the resection or staple line) may include a diameter of from about 1 cm to about 3 cm near the first landmark (e.g., the IA), from about 2 cm to about 6 cm near a second landmark (e.g., a pylorus) of the stomach, and from about 0 cm to about 2 cm near a third landmark (e.g., a gastroesophageal junction (GEJ) or GE junction) of the stomach.

In an example, the second medical device 20 may be positioned before the first medical device. That is, the surgeon may position the second medical device on the exterior of the stomach to create a lateral boundary of a potential resultant sleeve as described herein and my then insert the first medical device 10 and create the additional boundaries at the landmarks 40a, 40b respectively as described herein.

Figure 7:
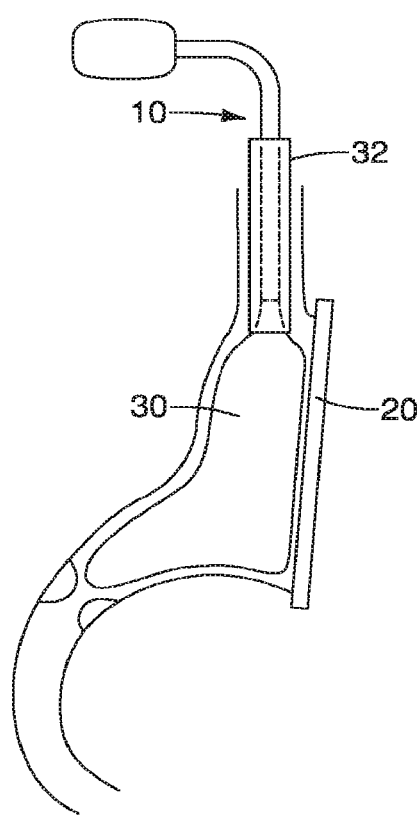
FIG. 7 depicts a front view of a stomach with the compliant balloon of FIG. 5 shown inflated.
Figure 8:
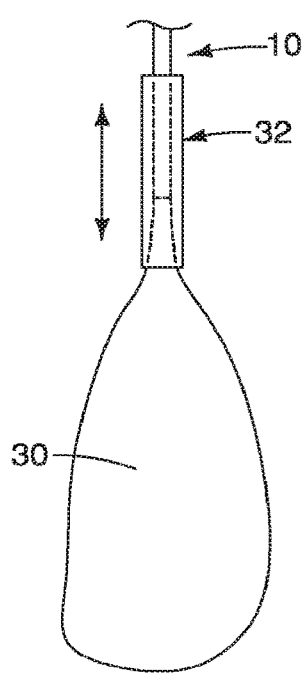
FIG. 8 depicts a front view of the compliant balloon shown in FIG. 5 shown in cooperation with the sheath shown in FIG. 6 according to one embodiment.

FIGS. 5-18 depict additional or alternative devices that may be used to measure sleeve volume in one or more examples herein including the method or procedure described with reference to FIGS. 3-4. As shown in FIGS. 5-8, in an example, rather than occluding the gastric outlet and the gastric inlet (e.g., at the landmarks 40a, 40b as described above), the first medical device 10 may include a compliant balloon 30 that may be used to fill the space of the proposed or potential resultant sleeve (e.g., as shown in FIG. 7). The second medical device 20 may occlude the lateral border as described herein and the balloon may be filled until a desired pressure may reached at which point volume may be measured or assessed. In an additional or alternative example, a height of the compliant balloon may be adjusted with a sheath 32 as shown in FIGS. 7-8 so the balloon may be positioned distal to the landmark 40b or the esophagus and proximal to the landmark 40a or the pylorus as described herein. A pressure bag or elevation of an open syringe to a given height above the cricoid (e.g., 70 cm of water) may be used to assess the volume by the displacement recorded from the container into the proposed sleeve. This may be performed before or after stapling the stomach to assess volume of the sleeve pouch. According to an example, if done prior to stapling, the surgeon may have the ability to adjust the position of the stapler to achieve an optimal size and shape under pressure.

Figure 9:
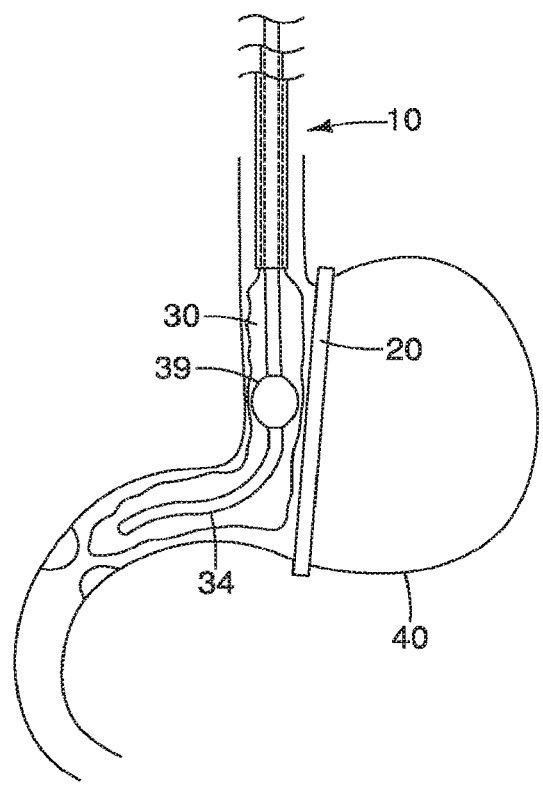
FIG. 9 depicts a front view of a stomach shown with a compliant balloon in cooperation with a second wider balloon according to one embodiment.
Figure 10:
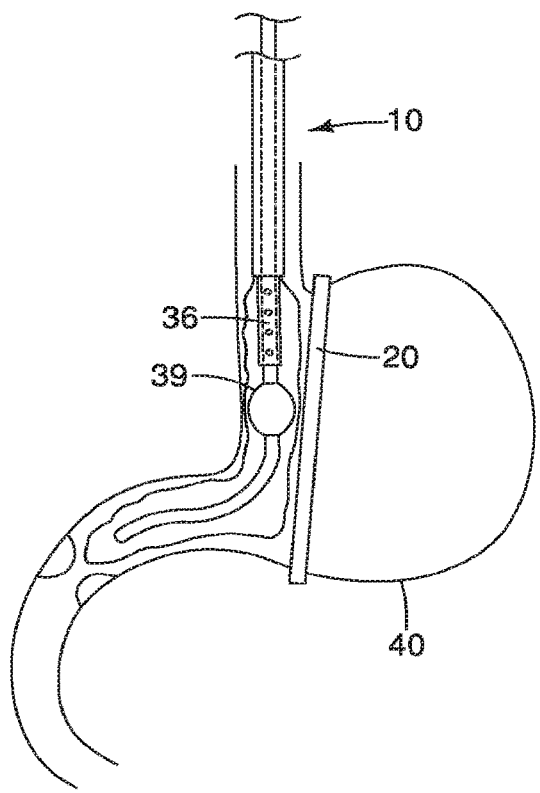
FIG. 10 depicts a front view of the compliant balloon and the second wider balloon shown in FIG. 9 in combination with a cylindrical balloon according to one embodiment.
Figure 11:
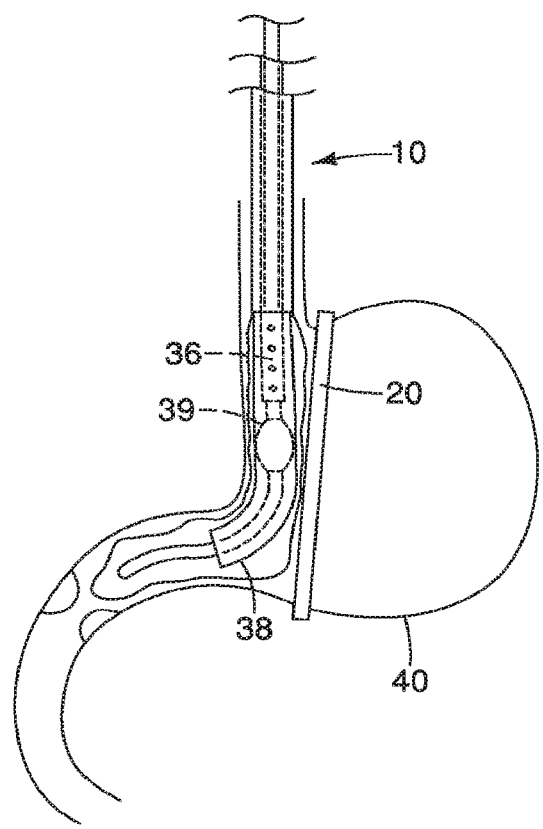
FIG. 11 depicts a front view of the compliant balloon and the second wider balloon shown in FIG. 9, the cylindrical balloon shown in FIG. 10, and a second cylindrical balloon according to one embodiment.

Further, in an example, as shown in FIGS. 9-11, the first medical device 10 may include a compliant balloon 30 that may be combined with a two-diameter tube, a three-diameter tube, a balloon tipped orogastric calibration tube, and/or the like. In this example, a desired position from the incisura *angularis* (IA) may be obtained and volume may be measured in the same orogastric calibration tube 34 as shown in FIG. 9. An additional cylindrical balloon 36 and/or 38 may be positioned along the upper portion and lower portion of the orogastric tube with a wider balloon 39 at the incisura *angularis* and a compliant balloon 30 therearound to measure volume of the sleeve as shown in FIGS. 10-11. In an example, the medical device 20 may include a single cartridge sleeve gastrectomy stapler that may be positioned alongside points of the stomach (e.g., points 1, 2, and 3 as described in U.S. patent application Ser. No. 14/846,764 or PCT/US15/48740, the contents of which are incorporated herein in their entirety by reference). Additionally, the balloon and tubes may enable different fill times to measure volume. For example, the balloon adjacent the incisura *angularis* (e.g., 40c) may fill first, the first and/or second cylindrical balloons may fill second and third, and the large compliant balloon may fill last or fourth. The timing of the balloon filling may accomplished by the size of the openings or apertures (e.g., such as 12) to the lumen of the orogastric tube. The largest opening will fill first as it has the least resistance to flow. The balloon adjacent the incisura *angularis* may have the largest opening to the tube lumen and may fill first. The cylindrical balloons may have multiple openings that may have more resistance than the incisura *angularis* but less resistance than the volume balloon and may fill second and/or third. The volume balloon, even though more compliant, may fill after the incisura *angularis* and cylindrical balloons may be filled to capacity and are under pressure. Thus, the surgeon may be able to position the stapler at safe distances from key landmarks then measure volume. The volume may be measured by displacement or pressure as described herein.

Figure 12:
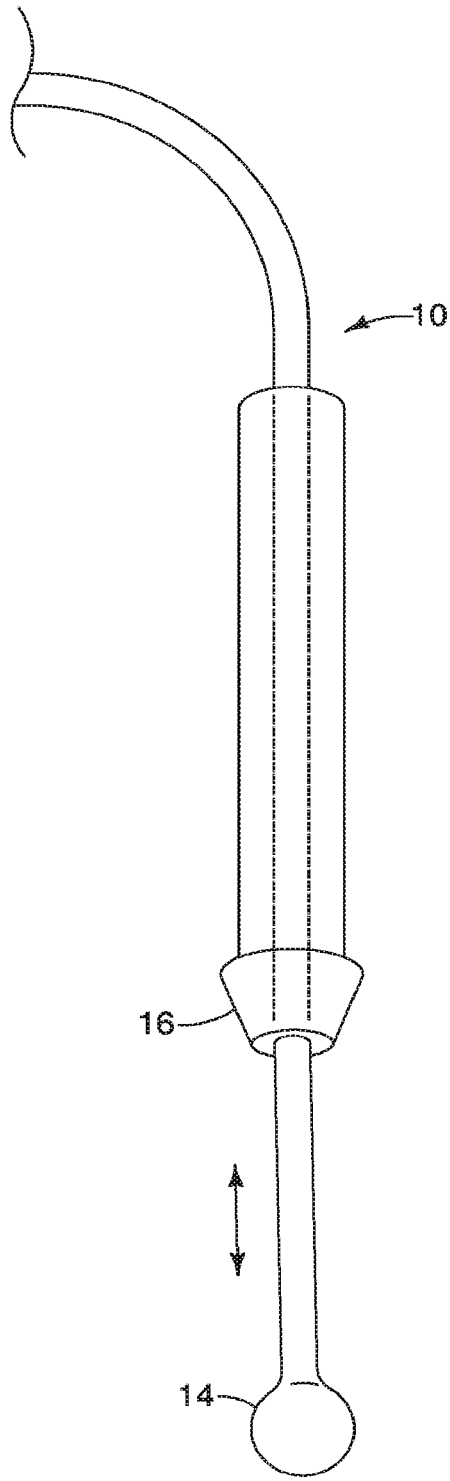
FIG. 12 depicts a front perspective view of a medical device having a first occlusion portion and a second occlusion portion according to one embodiment.
Figure 13:
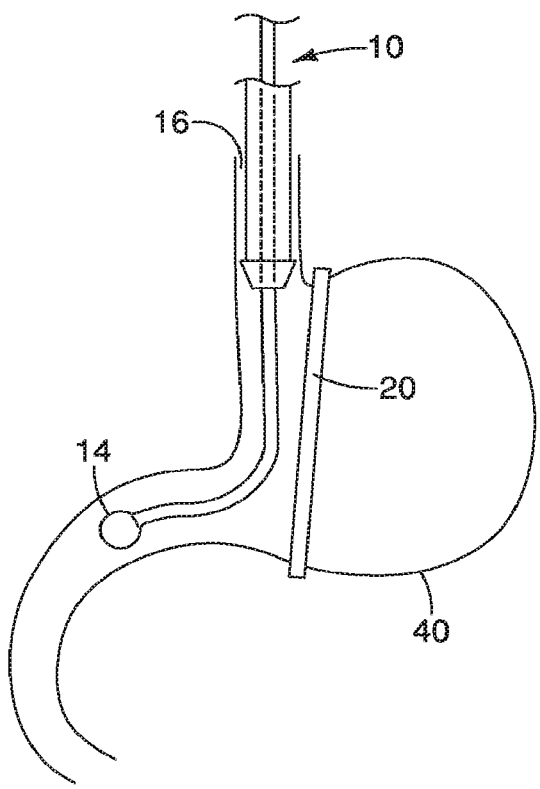
FIG. 13 depicts a front view of a stomach shown with the medical device of FIG. 12 according to one embodiment.

As shown in FIG. 12-13, the second occlusion device 16 may be integrated or included in the first medical device 10. For example, as shown, the first medical device 10 may include a first tube with the first occlusion device 16 and a second tube that may be placed over the first tube that may include the second occlusion device 16 such that the first and second tubes may slides proximally and distally with respect to each other to position the first occlusion device 14 at the first landmark 40a and the second occlusion device 16 at the landmark 40b as described herein.

Figure 14:
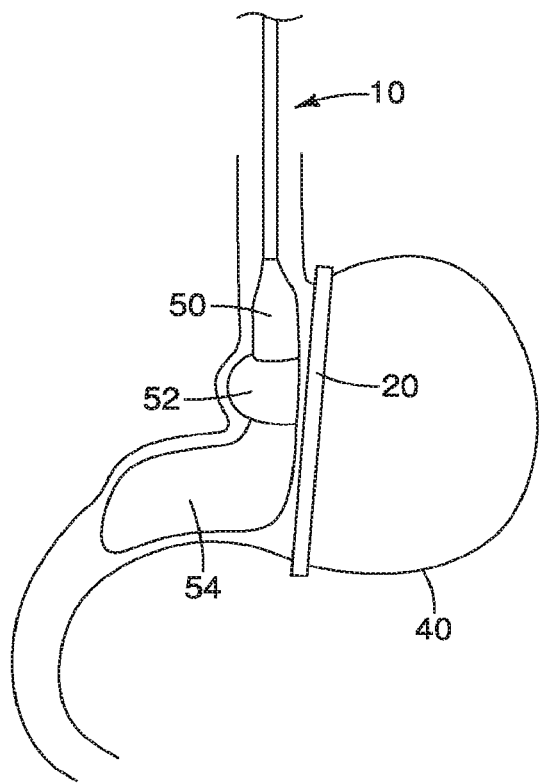
FIG. 14 depicts a front view of a stomach shown with a medical device having a plurality of balloons according to one embodiment.
Figure 15:
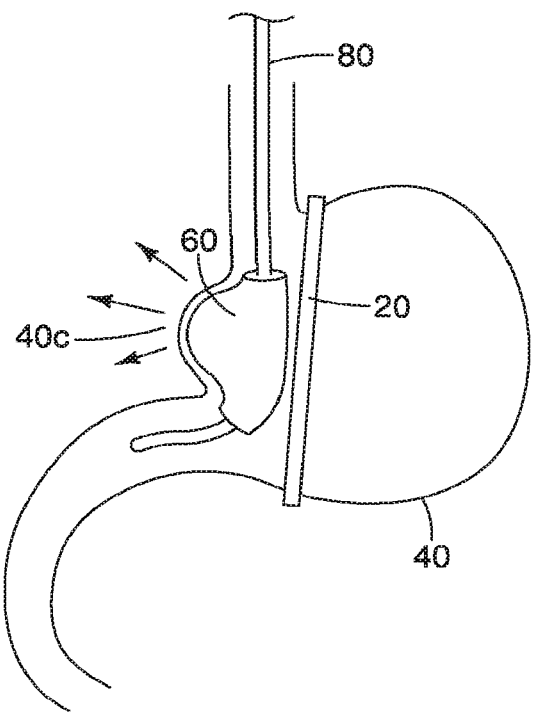
FIG. 15 depicts a front view of a stomach shown with a medical device having a first region with a constant diameter and a second region with a diameter great then the diameter of the first region.
Figure 16:
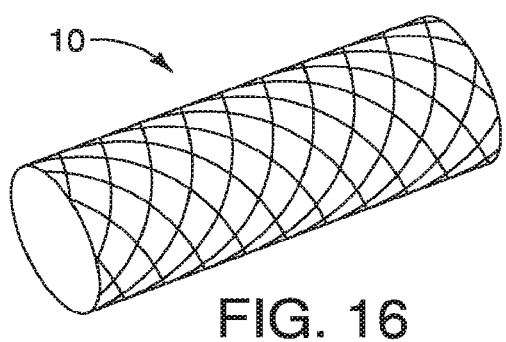
FIG. 16 depicts a partial perspective view of a region of a medical device having a constant diameter according to one embodiment.
Figure 17:
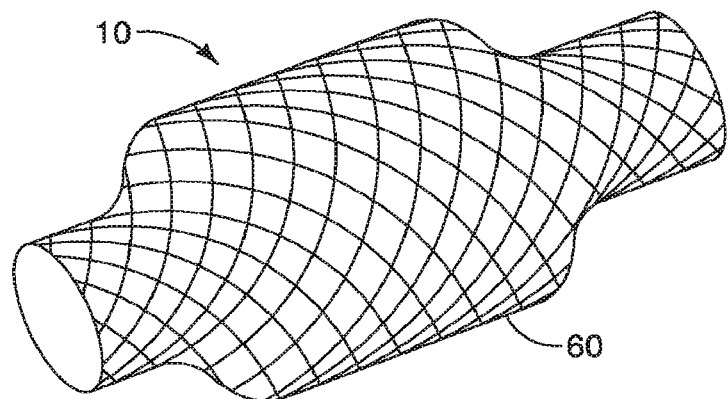
FIG. 17 depicts a partial perspective view of a medical device having a first region with a first diameter and a second region with a second diameter, where the second diameter is great than the first diameter, according to one embodiment.
Figure 18:
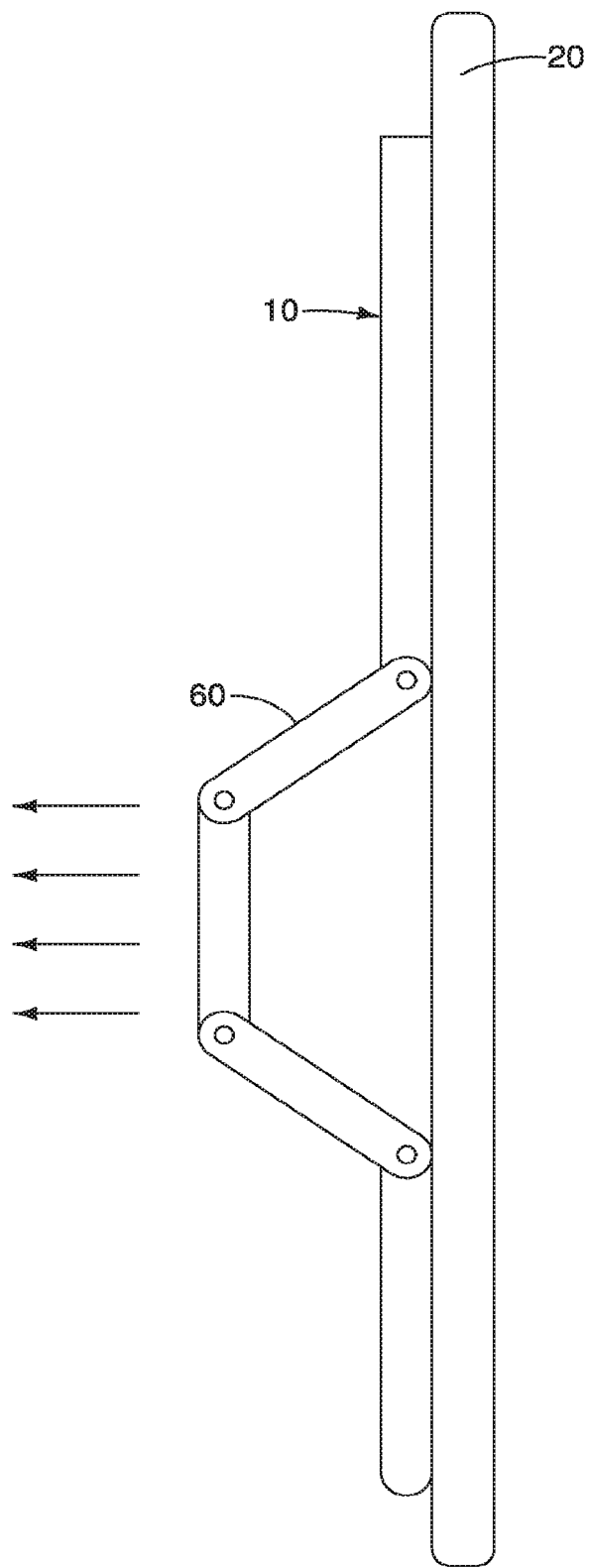
FIG. 18 depicts a front view of a medical device having a laterally expandable region according to one embodiment.

In an example, as shown in FIG. 14, the first medical device 10 may include a set of at balloons 50, 52, and/or 54 that may be compliant such that they may be inflated to measure volume and also may not exceed a shape of a resultant sleeve desired by the surgeon. As shown, the first medical device 10 that may include the balloons may be used with the second medical device 20 as described. Alternatively or additionally, in an example, the first medical device may include a non-compliant backbone along the edge adjacent to the second medical device 20 such that the second medical device 20 may not be used.

According to examples, the first medical device 10 described herein may also include one or more portions 60 that may be wider at a landmark 40c such as the IA of the stomach 40 as shown in FIGS. 15-18. For example, the first medical device 10 may include a constant diameter along a portion thereof and may have a wider diameter (e.g., after inflation, actuation, and/or the like) along the lesser curve or the landmark 40c (e.g., the IA).

Although examples herein may be described with respect to measuring volume, the examples may also be used with one or more of the examples described in U.S. patent application Ser. No. 14/846,764 or PCT/US15/48740, the contents of which are incorporated herein in their entirety by reference.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from a variety of metal and/or plastic materials.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method of performing a sleeve gastrectomy on a stomach of a patient, comprising:

positioning a first medical device in the interior of the stomach, the first medical device including a first occlusion device at a distal end thereof, the first medical device being positioned by inserting the first medical device into a mouth of the patient to access the interior of the stomach and positioning the first occlusion device at a landmark of the stomach, the first occlusion device defining a distal boundary of a potential resultant sleeve;

positioning a second occlusion device of the first medical device at another landmark of the stomach, the second occlusion device defining a proximal boundary of the potential resultant sleeve;

positioning a second medical device on the exterior of the stomach relative to the first medical device, the second medical device being configured to define a lateral boundary of the potential resultant sleeve and a path along which the sleeve gastrectomy may be performed; and determining a volume of the potential resultant sleeve, wherein determining the volume of the potential resultant sleeve further comprises one or more of the following:

filling the potential resultant sleeve to a predetermined pressure with fluid or gas, the fluid or gas configured to be trapped in the potential resultant sleeve by the distal, proximal, and lateral boundaries created by the first occlusion device, the second occlusion device, and the second medical device; and measuring the volume of the potential resultant sleeve at the predetermined pressure.

2. The method of claim 1, further comprising performing the sleeve gastrectomy along the path created by the second medical device, if based on the determination, the volume of the potential resultant sleeve may be a desired or suitable volume for a resected resultant sleeve.

3. The method of claim 1, further comprising adjusting the second medical device laterally if, based on the determination, the volume of the potential resultant sleeve may be too low or too high, and re-determining the volume of the potential resultant sleeve.

4. The method of claim 1, wherein the second medical device may be a clamp.

5. The method of claim 1, wherein the second medical device may be a stapler.

6. The method of claim 1, wherein the first medical device may include a medical tube.

7. The method of claim 1, wherein the first occlusion device may be a balloon.

8. The method of claim 1, wherein the second occlusion device is integrated or included in the first medical device.

9. The method of claim 1, wherein the second occlusion device is a clamp or an elastomeric band.

10. The method of claim 1, wherein the first medical device comprises a first portion with a first, constant diameter and a second portion with a second diameter, the second diameter being different from the first, constant diameter.

11. A medical device for a sleeve gastrectomy comprising:

a first medical device comprising at least a first occlusion device at a distal end thereof, the first medical device being configured to be inserted into an interior of a stomach and the first occlusion device being configured to be positioned at a landmark thereof to occlude a portion of the stomach and define a distal boundary of a potential resultant sleeve;

a second occlusion device, the second occlusion device being configured to be inserted into the interior of the stomach or positioned on an exterior of the stomach, the second occlusion device being configured to be positioned at another landmark of the stomach to occlude another portion of the stomach and define a proximal boundary of the potential resultant sleeve; and a second medical device being configured to be positioned on the exterior of the stomach relative to the first medical device, the second medical device being configured to define a lateral boundary and a path along which the sleeve gastrectomy may be performed, the lateral boundary along with the proximal and distal boundaries and occlusion thereof being configured to enable a measurement of a volume of the potential resultant sleeve, wherein the volume of the potential resultant sleeve may be configured to be determined by one or more of the following:

filling the potential resultant sleeve to a predetermined pressure with fluid or gas via the first medical device, the fluid or gas being configured to be trapped into the potential resultant sleeve by the distal, proximal, and lateral boundaries created by the first occlusion device, the second occlusion device, and the second medical device respectively; and measuring the volume of the potential resultant sleeve at the predetermined pressure.

12. The device of claim 11, wherein the second medical device is a clamp.

13. The device of claim 11, wherein the second medical device is a stapler.

14. The device of claim 11, wherein the first occlusion device is a balloon.

15. The device of claim 11, wherein the second occlusion device is integrated or included in the first medical device.

16. The device of claim 11, wherein the second occlusion device is a clamp or an elastomeric band.

17. The device of claim 11, wherein the first medical device comprises a first portion with a first, constant diameter and a second portion with a second diameter, the second diameter being different from the first, constant diameter.

* * * * *